United States Patent
Jiao et al.

(10) Patent No.: US 11,299,461 B2
(45) Date of Patent: Apr. 12, 2022

(54) PYRIDIN-2-YL ALKYLAMINO SUBSTITUTED HYDROXAMIC ACID AND USES THEREOF

(71) Applicant: HAWAII BIOTECH, INC., Honolulu, HI (US)

(72) Inventors: Guan-Sheng Jiao, Aiea, HI (US); Seong Jin Kim, Honolulu, HI (US); Alan T. Johnson, Kaneohe, HI (US)

(73) Assignee: HAWAII BIOTECH, INC., Honolulu, HI (US)

(*) Notice: Subject to any disclaimer, the term of this patent is extended or adjusted under 35 U.S.C. 154(b) by 0 days.

(21) Appl. No.: 16/979,503

(22) PCT Filed: Mar. 12, 2019

(86) PCT No.: PCT/US2019/021803
§ 371 (c)(1),
(2) Date: Sep. 9, 2020

(87) PCT Pub. No.: WO2019/178063
PCT Pub. Date: Sep. 19, 2019

(65) Prior Publication Data
US 2021/0371383 A1    Dec. 2, 2021

Related U.S. Application Data

(60) Provisional application No. 62/641,620, filed on Mar. 12, 2018.

(51) Int. Cl.
C07D 213/54    (2006.01)
C07D 213/65    (2006.01)
C07D 213/61    (2006.01)

(52) U.S. Cl.
CPC ......... C07D 213/65 (2013.01); C07D 213/54 (2013.01); C07D 213/61 (2013.01)

(58) Field of Classification Search
CPC ... C07D 213/54; C07D 213/61; C07D 213/65
USPC ....................................................... 514/351
See application file for complete search history.

(56) References Cited

U.S. PATENT DOCUMENTS 8,242,174 B2    8/2012    Johnson et al.
2008/0221132 A1    9/2008    Cai et al.

FOREIGN PATENT DOCUMENTS

WO    2005/027856 A2    3/2005
WO    2008/147480 A2    4/2008
WO    2008/094592 A1    8/2008

OTHER PUBLICATIONS

European Patent Office, Extended European Search Report issued in EP Patent Application No. 19767431.0, dated Jul. 5, 2021, pp. 1-9.
Alsfasser et al., Novel Building Blocks for Biomimetic Assemblies. Synthesis, Characterization, and Spectroscopic and Electrochemical Properties of New Bidentate Ligands Derived from Lysine and Cysteine and Their Complexes with Bis(2,2'-bipyridine)ruthenium(II), Inorg. Chem., 1996, pp. 628-636, vol. 35.
Patent Cooperation Treaty, International Search Report issued in PCT/US2019/021803, dated Jul. 9, 2019, pp. 1-4.
Moayeri et al., Small-Molecule Inhibitors of Lethal Factor Protease Activity Protect against Anthrax Infection, Jun. 17, 2013, pp. 4139-4145, Vo. 57(9).
Jiao et al., Antidotes to anthrax lethal factor intoxication. Part 1: Discovery of potent lethal factor inhibitors with in vivo efficacy, Bioorganic & Medicinal Chemistry Letters, 2010, pp. 6850-6853, vol. 20(22).
Kim et al., Antidotes to anthrax lethal factor intoxication. Part 2: Structural modifications leading to improved in vivo efficacy, Bioorganic & Medicinal Chemistry Letters, 2011, pp. 2030-2033, vol. 21(7).
Jiao et al., Antidotes to anthrax lethal factor intoxication. Part 3: Evaluation of core structures and further modifications to the C2-side chain, Bioorganic & Medicinal Chemistry Letters, 2012, pp. 2242-2246, vol. 22(6).

*Primary Examiner* — Niloofar Rahmani
(74) *Attorney, Agent, or Firm* — Pillsbury Winthrop Shaw Pittman LLP

(57) ABSTRACT

Compounds of formula I are provided:

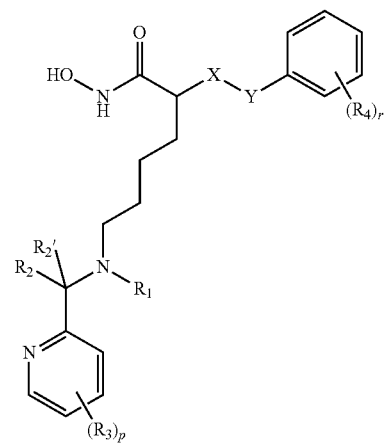

wherein X is NH, or $CH_2$, Y is a single bond, or —$CHR_5$—, $R_1$ is H, $C_1$-$C_4$ alkyl, or $C_1$-$C_4$ hydroxyalkyl, $R_2$ and $R_2'$ are each independently H, $C_1$-$C_4$ alkyl, or $C_1$-$C_4$ hydroxyalkyl, each $R_3$ is independently H, halo, —$CF_3$, $C_1$-$C_4$ alkyl, or $C_1$-$C_4$ alkoxy, $C_3$ perhaloalkyl, each $R_4$ is independently H, halo, or $C_1$-$C_4$ alkyl, $R_5$ is $C_1$-$C_4$ alkoxy, r is integer from 0 to 3; and p is integer from 0 to 3.

21 Claims, No Drawings

PYRIDIN-2-YL ALKYLAMINO SUBSTITUTED HYDROXAMIC ACID AND USES THEREOF

RELATED PATENT APPLICATIONS

This patent application is the National Phase of International Application No. PCT/US2019/021803, filed Mar. 12, 2019, which claims the benefit of U.S. Provisional Patent Application No. 62/641,620, filed Mar. 12, 2018, entitled PYRIDIN-2-YL ALKYLAMINO SUBSTITUTED HYDROXAMIC ACID AND USES THEREOF. The entire contents of the foregoing applications is incorporated herein by reference, including all text and tables.

STATEMENT OF GOVERNMENT SPONSORSHIP

This invention was made with government support under the grants U01 AI078067 and R01 AI104586 awarded by the National Institutes of Health, National Institute of Allergy and Infectious Diseases. The government has certain rights in the invention.

INTRODUCTION

The present disclosure relates to compounds and methods developed to treat exposure to toxins, such as those from *Bacillus anthracis* (*B. anthracis*). In particular, the present disclosure relates to hydroxamic acid compounds that serve as inhibitors of anthrax lethal factor, a key component of a binary toxin produced by *B. anthracis*.

*B. anthracis* is a gram-positive, spore-forming, rod-like bacterium that produces *B. anthracis* toxin and causes the disease anthrax. *B. anthracis* exists in two forms: as an active growing cell (called the vegetative form) or as a dormant spore. When a spore enters a mammal host, the internal environment of the host-rich in water, sugars, and amino acids-induces that spore to germinate into a vegetative cell that leads to disease. (Helgason, et al., *Applied and Environmental Microbiology* 2000, 66, 2627-2630; Weber, et al., *Antimicrob Agents and Chemotherapy* 1988, 32, 642-645; and Doganay, et al., *Scand. J. inf. Dis.* 1991, 23, 333-335 for further discussion of *Bacillus anthracis*.)

Two major exotoxins are produced by *B. anthracis*. These result from the combination of three secreted proteins: a receptor-binding component designated protective antigen (PA), and two enzymatic components termed edema factor (EF) and lethal factor (LF). (Mock, et al., *Annu. Rev. Microbiol.* 2001, 55, 647-71.) Edema factor (EF) and lethal factor (LF) each of which combines with protective antigen (PA) to form two binary toxins; edema toxin (ET) and lethal toxin (LT) respectively. In the early stages of disease these toxins act as virulence factors and suppress the immune system of the host allowing *B. anthracis* to establish infection. (Moayeri, et al., *Mol. Aspects Med.* 2009, 30, 439). In later stages, high levels of LT and ET contribute to the death of the host. Recent studies in mice indicate that the cardiovascular system is the major target of LT while the liver is the primary target of ET. (Liu, S.; et al al. *Nature* 2013, 501, 63.)

The protein EF is a $Ca^{2+}$/calmodulin-dependant adenylate cyclase that increases cytosolic cAMP and also interferes with cell signaling. (Leppla, S. H. *Proc. Nat. Acad. Sci. U.S.A.* 1982, 79, 3162; Tang, W.-J.; Guo, Q. *Mol. Aspects Med.* 2009, 30, 423.) The protein LF acts as a $Zn^{2+}$-dependent metalloproteinase and disrupts cell signaling pathways by cleavage of MEK proteins. (Duesbury, N. S.; Webb, C. P.; Leppla, S. H.; Gordon, V. M.; Copeland, T. D.; Ahn, N. G.; Oskarsson, M. K.; Fukasawa, K.; Paull, K. D.; Vande Woude, G. F. *Science* 1998, 280, 734; Vitale, G.; Bernardi, L.; Napolitani, G.; Mock, M.; Montecucco, C. *Biochem. J.* 2000, 352, 739.) PA transports EF and LF into cells where they act as potent virulence factors and contribute to the pathogenesis of the disease. (Collier, R. J.; Young, J. A. *Annu. Rev. Cell Dev. Bio.* 2003, 19, 45.) The details of how EF and LF act to suppress the immune system, support dissemination of the bacteria, and contribute to the lethality of the disease are beginning to be revealed (Moayeri, M.; Leppla, S. H. *Mol. Aspects Med.* 2009, 30, 439) and suggest that inhibiting the activity of these toxins could lead to an increase in survival of the infected host.

Anthrax is classified depending on the route of exposure. The most common form in humans is cutaneous anthrax, associated with skin lesions and is manageable with antibiotics. Gastrointestinal anthrax causes a much more serious systemic disease but primarily affects livestock that have ingested food contaminated with the bacterial spores. Pulmonary (inhalation) anthrax is the most fatal form of anthrax which results from inhaling airborne spores. Pulmonary anthrax can be asymptomatic for several weeks as lung macrophages and dendritic cells engulf and kill most inhaled spores; however, a fraction of the spores may survive within the alveolar macrophages and are transported to tracheobronchial and mediastinal lymph nodes and germinate, causing fulminant disease characterized by respiratory impairment, shock and widespread hemorrhage. (Male, et al., *Scientific Reports* 2017, 7, 3104.) While most *B. anthracis* strains are sensitive to a broad range of antibiotics such as ciprofloxacin, penicillin G procaine (penicillin), or doxycycline, the therapeutic benefit antibiotics dramatically decrease when administered in the symptomatic stage of the disease due to the accumulation of the bacterial toxins, and are ineffective in the fulminate stage when death usually occurs within 24 hours. (Holty, et al. *Ann Intern Med.* 2006, 144, 270-80.)

Anthrax is currently considered one of the most serious bioterrorism threats. Beginning in the second half of the $20^{th}$ Century, *B. anthracis* was developed by several countries as part of their biological weapons programs. Autonomous groups have also demonstrated intent to use *B. anthracis* in acts of terrorism. Given the potential for mass casualties by using anthrax as a weapon of bioterrorism, there exists a need to discover new compounds which act as inhibitors of the anthrax toxins and therefore can effectively treat the *B. anthracis* infection.

The present disclosure represents a further advance in the field by providing hydroxamic acid derivatives of pyridin-2-yl alkylamines which are useful to treat anthrax poisoning.

SUMMARY

Disclosed herein are pyridin-2-yl alkylamino substituted hydroxamic acid compounds having an inhibitory effect on LF, the metalloproteinase component of anthrax lethal toxin. The disclosure relates to the use of such compounds for treating, preventing, inhibiting and/or diminishing the symptoms of *B. anthracis* infection. Also provided are pharmaceutical compositions thereof, methods of preparation thereof, and methods of use thereof.

DETAILED DESCRIPTION

In some aspects, there are provided compounds of formula I:

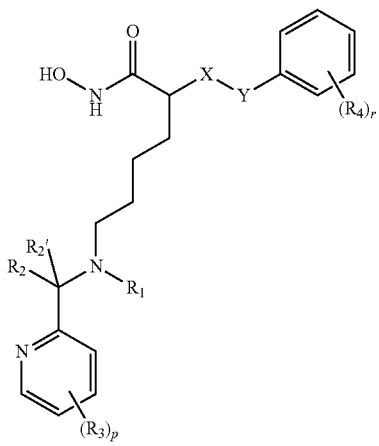

wherein
X is NH or $CH_2$;
Y is single bond, or $—CHR_5—$;
$R_1$ is H, $C_1$-$C_4$ alkyl, or $C_1$-$C_4$ hydroxyalkyl;
$R_2$ and $R_2'$ are each independently H, $C_1$-$C_4$ alkyl, or $C_1$-$C_4$ hydroxyalkyl;
each $R_3$ is independently H, halo, $C_1$-$C_4$ alkyl, $C_1$-$C_4$ alkoxy, $C_3$ perhaloalkyl;
each $R_4$ is independently H, halo, or $C_1$-$C_4$ alkyl;
$R_5$ is $C_1$-$C_4$ alkoxy; and
r and p are each independently integers from 0 to 3.

In some embodiments, X is NH. In some embodiments, X is $CH_2$.

In some embodiments, Y is a single bond. In some embodiments, Y is $—CH_2—$. In some embodiments, Y is $—CHR_5—$. In some embodiments, Y is $—CHOCH_3—$.

In some embodiments, Y is $—CHOCH_2CH_3—$.

In some embodiments, $R_1$ is H. In some embodiments, $R_1$ is $C_1$-$C_4$ alkyl. In further embodiments, $R_1$ is methyl, ethyl, isopropyl (iPr), or t-butyl. In some embodiments, $R_1$ is $C_1$-$C_4$ hydroxyalkyl. In further embodiments, $R_1$ is $CH_2CH_2OH$, or $—CH_2CH_2CH_2OH$ In some embodiments, one of $R_2$ and $R_2'$ is H. In some embodiments, both $R_2$ and $R_2'$ are H. In some embodiments, one of $R_2$ and $R_2'$ is H and the other one of $R_2$ and $R_2'$ is $C_1$-$C_4$ alkyl. In some embodiments, one of $R_2$ and $R_2'$ is $C_1$-$C_4$ hydroxyalkyl.

In some embodiments, the pyridine-2-yl moiety is unsubstituted (i.e., p=0). In some embodiments, the pyridine-2-yl moiety is substituted with one $R_3$ (i.e., p=1). In some embodiments, the pyridine-2-yl moiety is substituted with two $R_3$ (i.e., p=2). In some embodiments, the pyridine-2-yl moiety is substituted with three $R_3$ (i.e., p=3). In some embodiments, $R_3$ is substituted at the C-3 position of pyridine-2-yl. In some embodiments, $R_3$ is substituted at the C-4 position of pyridine-2-yl. In some embodiments, $R_3$ is substituted at the C-5 position of pyridine-2-yl. In some embodiments, $R_3$ is substituted at the C-6 position of pyridine-2-yl. In some embodiments, two $R_3$ are substituted at the C-3 and C-5 positions of pyridine-2-yl.

In some embodiments, one of $R_3$ is $C_1$-$C_4$ alkyl. In further embodiments, one of $R_3$ is methyl. In some embodiments, one of $R_3$ is $—CF_3$. In some embodiments, one of $R_3$ is halo. In further embodiments, one of $R_3$ is F, Cl, or Br. In some embodiments, one of $R_3$ is $C_1$-$C_4$ alkoxy. In further embodiments, one of $R_3$ is methoxy. In some embodiments, one of $R_3$ is $—CF_3$.

In some embodiments, when p is 2 or 3, at least two $R_3$ are the same. In some embodiments, all $R_3$ are different. In some embodiments, at least two $R_3$ are halo. In further embodiments, at least two $R_3$ are F. In further embodiments, at least two $R_3$ are $C_1$. In further embodiments, the at least two $R_3$ are F and Cl. In some embodiments, the at least two $R_3$ are halo and $C_1$-$C_4$ alkyl. In further embodiments, the at least two $R_3$ are ethyl and Cl. In further embodiments, the at least two $R_3$ are methyl and F.

In some embodiments, at least one of $R_4$ is halo. In some embodiments, at least one of $R_4$ is $C_1$-$C_4$ alkyl. In further embodiments, at least one of $R_4$ is methyl. In some embodiments, at least two of $R_4$ are $C_1$-$C_4$ alkyl. In further embodiments, at least two of $R_4$ are methyl. In some embodiments, at least two of $R_4$ are halo. In some embodiments, $R_4$ are F, Cl, methyl, or mixtures thereof.

In some embodiments, one of $R_4$ is F and is substituted at the para-position. In some embodiments, one of $R_4$ is F and is substituted at the meta-position. In some embodiments, one of $R_4$ is methyl and is substituted at the meta-position. In some embodiments, two of $R_4$ are methyl and are substituted at the meta-positions. In some embodiments, one of $R_4$ is $C_1$ and is substituted at the meta-position. In some embodiments, two of $R_4$ are $C_1$ and are substituted at the meta-positions.

In some aspects, there are provided compounds of formula II:

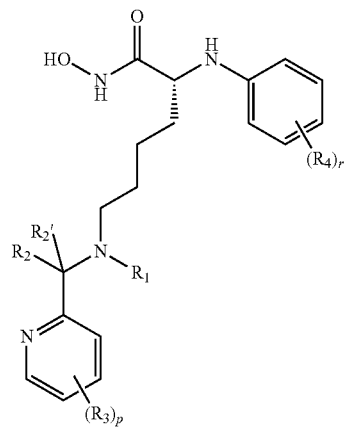

wherein each of variables is as defined herein.

In some aspects, there are provided compounds of formula III:

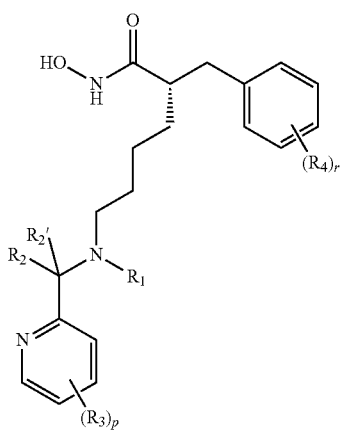

wherein each of variables is as defined herein.

In some aspects, there are provided compounds of formula IV:

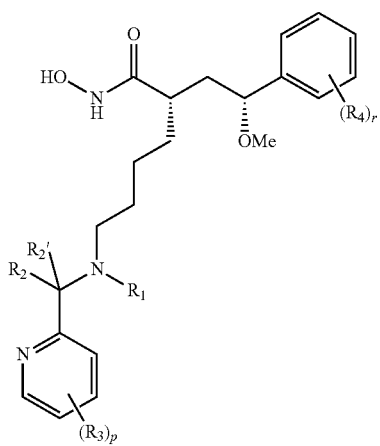

wherein each of variables is as defined herein.

In some embodiments, the disclosure provides one or more of the following compounds 1 to 58 of Tables 2-4 below, or any pharmaceutically acceptable salt, ester, prodrug, homolog, tautomer, stereoisomer, isotope, hydrate, or solvate thereof.

Pharmaceutical Composition

In some aspects, the aforementioned compounds may be formulated in pharmaceutical compositions comprising the compound along with a pharmaceutically acceptable carrier, in accordance with standard pharmaceutical practice as a pharmaceutical composition.

In certain embodiments, there are provided a pharmaceutical composition comprising a compound of Formula I-IV, or any pharmaceutically acceptable salt, ester, prodrug, homolog, tautomer, stereoisomer, isotope, or hydrate, or solvate thereof, together with at least one pharmaceutically acceptable carrier, diluent or excipient. The particular carrier employed in these pharmaceutical compositions may vary depending upon the type of administration desired (e.g., intravenous, oral, topical, suppository, or parenteral).

A "salt" includes an organic compound such as a carboxylic acid, a sulfonic acid, or an amine, in ionic form, in combination with a counterion. For example, acids in their anionic form can form salts with cations such as metal cations, for example sodium, potassium, and the like; amines may take the form of ammonium salts such as $NH_4^+$ via mineral acids or other organic acids or as cations of various alkylamines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds disclosed herein may take the form of salts. The term "salts" embraces addition salts of free acids or free bases of the compounds disclosed. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which may have utility in processes of synthesis, purification or formulation of compounds disclosed herein.

Typical compositions include a compound as disclosed herein in a pharmaceutically acceptable excipient which can be a carrier or a diluent. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example, contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents which do not deleteriously react with the active compounds. Such additives can include wetting agents, emulsifying and suspending agents, salt for influencing osmotic pressure, buffers and/or coloring substances, preserving agents, sweetening agents or flavoring agents. The compositions can also be sterilized if desired.

Modes of Administration

The compounds of the disclosure may be administered to the subject in a therapeutically effective amount orally, intravenously, subcutaneously, intramuscularly or any other method known to those skilled in the art (e.g., rectal, parenteral). For oral administration, the compositions may be in the form of compressed tablets, dragees or capsules prepared by conventional means using known supports and excipients such as binders, fillers, lubricants or disintegration agents; alternatively they may be in the form of solutions, syrups or suspensions.

For administration in the form of injectable solutes, the compound may be prepared as a solution or suspension capable of being administered by injection. A suitable pharmaceutical composition may be made for sterile injection containing between 1 and 50% w/w of the compounds used in the disclosure.

In certain cases, it may be useful to formulate the compounds of the disclosure in suppository form or as extended release formulation for deposit under the skin or intramuscular injection. For each type of administration appropriate pharmaceutical excipients are likely to be added to the drug. The nature of such excipients for each type of systemic administration is well known in the art and need not be described here further.

A useful therapeutic or prophylactic concentration will vary from with the precise identity of the drug, with the severity of the anthrax infection being treated and the subject's susceptibility to treatment. Accordingly, no single concentration will be uniformly useful, but will require modification depending on the particularities of each situation. However, it is anticipated that an amount between 1.0 and 10 mg per kg of body weight per day will affect a therapeutic result.

Suitable subjects for the administration of the formulations herein include primates, humans and other animals, particularly humans and domesticated animals such as cats, rabbits and dogs.

Method of Treatments

In some aspects, the compounds of formulas I-IV or pharmaceutical acceptable salts, enantiomers, diastereomers or prodrug or mixture thereof may be useful for the treatment or prophylaxis of an *B. anthracis* infection, such as anthrax.

The compounds of formula I may be used alone, or in combination with one or more active agent to effectively treat a *B. anthracis* infection. Examples of active agents include, but are not limited to, antibacterial agents including ciprofloxacin, penicillin, and doxycycline and also biologic agents such as anti-PA antibodies including raxibacumab, obiltoxaximab, and AIG.

In embodiments, the disclosure provides the use of a compound of formulas I-IV for the production of a medicament for the treatment or prophylaxis of an *B. anthracis* infection, such as anthrax. In embodiments, the disclosure provides the use of a compound of formula I for the production of a medicament for inhibiting LF.

In embodiments, a method is provided for the preparation of a medicament useful for the treatment or prophylaxis of a *B. anthracis* infection, where the medicament comprising a pharmaceutical composition disclosed herein.

In embodiments, there are provided methods of treating a subject exposed to a *B. anthracis* toxin by administering to the subject a pharmaceutical composition comprising a compound according to one or more of the previous embodiments. In these embodiments, a method is provided for inhibiting the activity of LF.

Determining Biological Activity

As noted above, the often lethal results of anthrax poisoning are caused by a toxin that is released by *B. anthracis* within the host. The toxin includes three proteins, one of which is a zinc-dependent metalloprotease enzyme (LF) that cleaves near the N termini of several MAP kinase kinase enzymes (MKKS) of the host. It is this disruption of key signaling pathways mediated by the host MKK enzymes that result in the severe and often lethal results of infection by the bacteria.

An assay for identifying and measuring the effectiveness of potential drugs to treat anthrax poisoning is based on measuring the inhibitory effect of the candidate compound on the lethal factor enzyme. The procedure used to measure the potential efficiency of the compounds disclosed herein is based, in a somewhat modified form, on a previously described peptide-based fluorescence resonance energy transfer assay. (Cummings et al., *Proc. Nat. Acad. Sci. U.S.A.* 2002, 99, 6603), expressly incorporated herein by reference. The assay employs a fluorogenic peptide substrate which is incubated with the lethal factor enzyme in the presence of the inhibitor and the level of lethal factor inhibition determined by measuring the fluorescence intensity of the cleaved substrate. A description of the actual assay conditions used for evaluating the compounds disclosed herein is provided below.

Method of Making

Embodiments herein provide methods for the synthesis of certain compounds including compounds of the disclosure. In certain other embodiments, the disclosure provides certain intermediate compounds associated with such methods of synthesis.

A number of embodiments have been described. Nevertheless, it will be understood that various modifications may be made without departing from the spirit and scope of these embodiments. Accordingly, the following examples are intended to illustrate but not limit the scope of the embodiments described in the claims.

General Synthetic Methods for Preparing Compounds

Molecular embodiments disclosed herein can be synthesized using standard synthetic techniques known to those of skill in the art. Compounds of the present disclosure can be synthesized using the general synthetic procedures set forth in Schemes 1-5.

Scheme 1 Synthesis of compounds of 1-8

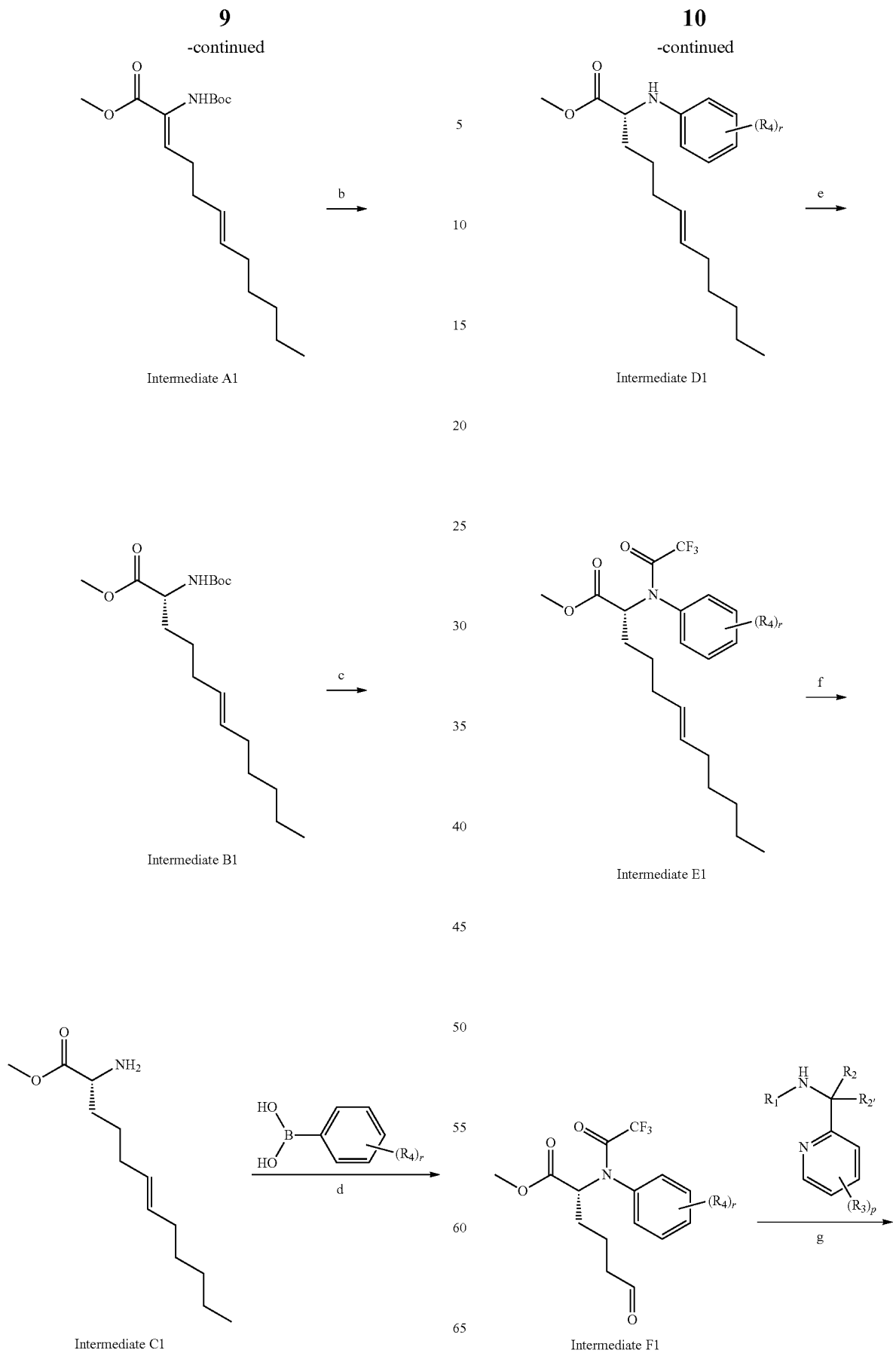

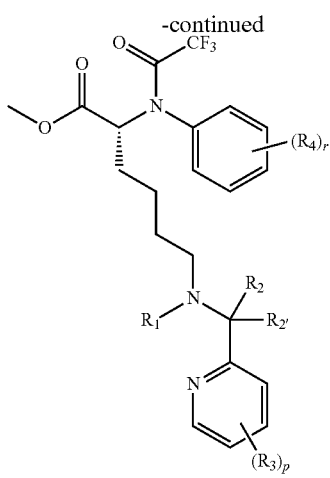

Intermediate G1

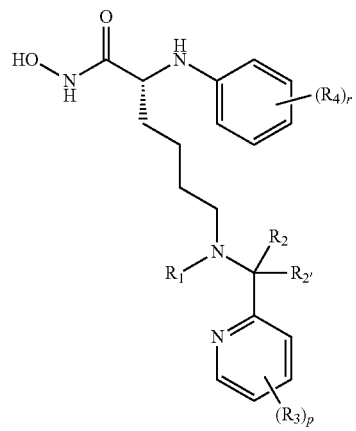

Compounds
1 to 8

Reagents and conditions: (a) tetramethylguanidine, DCM, 25° C.; (b) H₂, (R,R)-Et-DuPHOS, EtOH, 25° C.; (c) TFA, DCM, 25° C.; (d) O₂, Cu(OAc)₂, Et₃N, DCM, 25° C.; (e) (CF₃CO)₂O, DIEA, DCM, 25° C.; (f) O₃, Ph₃P, DCM, -78° C.; (g) NaBH(OAc)₃, Et₃N, DCE, 25° C.; (h) 50% NH₂OH—H₂O, KCN, THF, MeOH, 25° C.

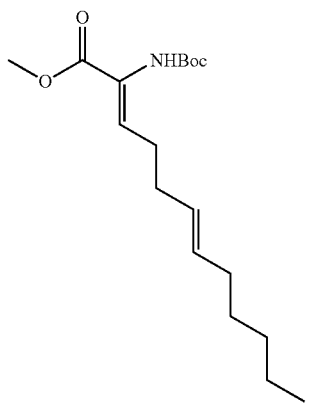 [SMILES: CCCCC/C=C/CC/C=C(\NC(=O)OC(C)(C)C)C(=O)OC]

Methyl (2Z,6E)-2-((tert-butoxycarbonyl)amino)dodeca-2,6-dienoate (Intermediate A1). To a solution of methyl 2-((tert-butoxycarbonyl)amino)-2-(dimethoxyphosphoryl)acetate (10.000 g, 33.643 mmol) and (E)-dec-4-enal (4.941 g, 32.041 mmol) in 100 mL of DCM, tetramethylguanidine (5.6 mL, 44.537 mmol) was added. After stirring at room temperature for overnight, the reaction mixture was concentrated under reduced pressure. The resulting residue was purified by column chromatography (silica gel) eluting with 0-15% ethyl acetate/hexanes to give the desired product as a colorless oil (10.323 g, 99% yield). GC-MS (Method C): $t_R$=9.2 min; M⁺: 325.

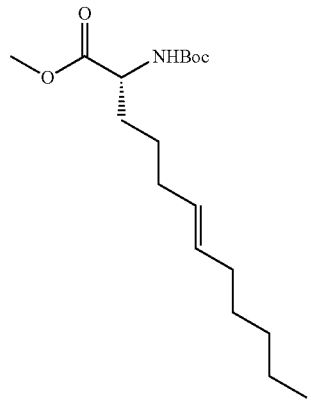 [SMILES: CCCCC/C=C/CCC[C@@H](NC(=O)OC(C)(C)C)C(=O)OC]

Methyl (R,E)-2-((tert-butoxycarbonyl)amino)dodec-6-enoate (Intermediate B1). To a solution of methyl (2Z,6E)-2-((tert-butoxycarbonyl)amino)dodeca-2,6-dienoate (1.000 g, 3.073 mmol) in 30 mL of EtOH in a hydrogenation flask, (R,R)-Et-DuPHOS (0.044 g, 0.0614 mmol) was added. The flask was then placed on a hydrogenator and was evacuated under reduced pressure and back filled with hydrogen 5 times. After shaking under hydrogen at 30 Psi for 4 hours, the reaction mixture was concentrated under reduced pressure. The resulting residue was purified by column chromatography (silica gel) eluting with 0-30% ethyl acetate/hexanes to give the desired product as a colorless oil (0.848 g, 84% yield). GC-MS (Method C): $t_R$=8.9 min; M⁺: 327.

Methyl (R,E)-2-aminododec-6-enoate (Intermediate C1). To a solution of methyl (R,E)-2-((tert-butoxycarbonyl)amino)dodec-6-enoate (4.844 g, 14.793 mmol) in 40 mL of DCM, trifluoroacetic acid (40 mL) was added. After stirring at room temperature for 3 hours, the reaction mixture was concentrated under reduced pressure to give the desired product (TFA salt) as a brown gum which was azeotropically dried with toluene three times and used directly in the next step without further purification.

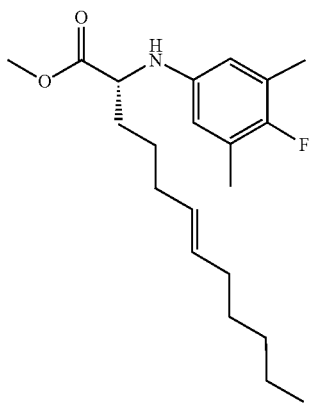

Methyl (R,E)-2-((4-fluoro-3,5-dimethylphenyl)amino)dodec-6-enoate (Example Intermediate D1). To a mixture of methyl (R,E)-2-aminododec-6-enoate trifluoroacetate (14.793 mmol directly from the previous step), (4-fluoro-3,5-dimethylphenyl)boronic acid (5.218 g, 31.065 mmol), and Cu(OAc)$_2$ (2.956 g, 16.272 mmol) in 120 mL of DCM, triethylamine (4.33 mL, 31.065 mmol) was added. After stirring at room temperature under O2 for 2 days, the reaction mixture was concentrated under reduced pressure. The resulting residue was purified by column chromatography (silica gel) eluting with 0-30% ethyl acetate/hexanes to give the desired product as a red oil (2.802 g, 54% yield). GC-MS (Method D): $t_R$=5.0 min; M$^+$: 349.

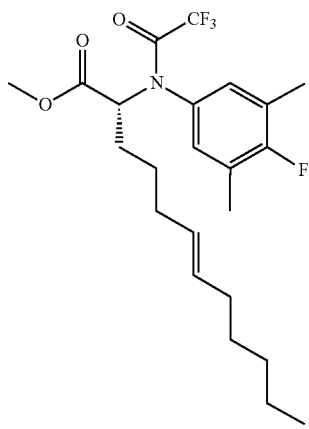

Methyl (R,E)-2-(2,2,2-trifluoro-N-(4-fluoro-3,5-dimethylphenyl)acetamido)dodec-6-enoate (Example Intermediate E1). To a solution of methyl (R,E)-2-((4-fluoro-3,5-dimethylphenyl)amino)dodec-6-enoate (2.802 g, 8.018 mmol) in 80 mL of DCM, trifluoroacetic anhydride (1.67 mL, 12.026 mmol) was added, followed by DIEA (4.19 mL, 24.054 mmol). After stirring at room temperature under N$_2$ for 3 hours, the reaction mixture was concentrated under reduced pressure. The resulting residue was purified by column chromatography (silica gel) eluting with 0-20% ethyl acetate/hexanes to give the desired product as a golden oil (3.121 g, 87% yield). GC-MS (Method D): $t_R$=4.4 min; M$^+$: 445.

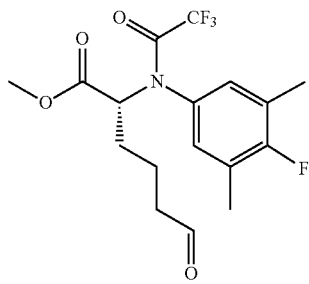

Methyl (R)-6-oxo-2-(2,2,2-trifluoro-N-(4-fluoro-3,5-dimethylphenyl)acetamido)hexanoate (Example Intermediate F1). A solution of methyl (R,E)-2-(2,2,2-trifluoro-N-(4-fluoro-3,5-dimethylphenyl)acetamido)dodec-6-enoate (3.121 g, 7.005 mmol) in 100 mL of DCM was cooled to −78° C. The solution was sparged with O2 for 10 minutes, then with O3 until the solution became blue. Then the solution was sparged with O2 again until the solution became clear. Triphenylphosphine (2.021 g, 7.706 mmol) was added. The reaction mixture was warmed to room temperature and stirred for overnight. The solvent was removed and the resulting residue was purified by column chromatography (silica gel) eluting with 0-30% ethyl acetate/hexanes to give the desired product as a yellow oil (2.104 g, 80% yield). GC-MS (Method D): $t_R$=3.1 min; M$^+$: 377.

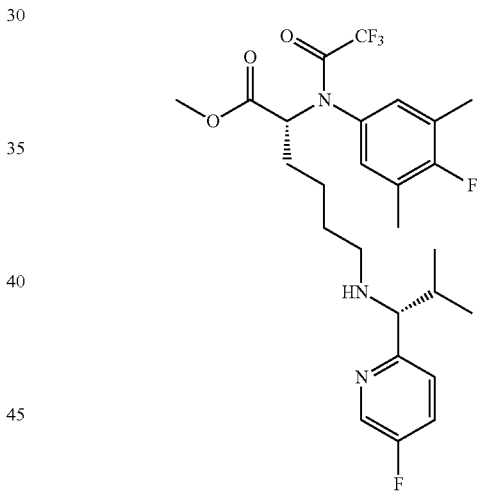

Methyl N2-(4-fluoro-3,5-dimethylphenyl)-N6-((R)-1-(5-fluoropyridin-2-yl)-2-methylpropyl)-N2-(2,2,2-trifluoroacetyl)-D-lysinate (Example Intermediate G1). To a mixture of methyl (R)-6-oxo-2-(2,2,2-trifluoro-N-(4-fluoro-3,5-dimethylphenyl)acetamido)hexanoate (0.150 g, 0.398 mmol) and (R)-1-(5-fluoropyridin-2-yl)-2-methylpropan-1-amine hydrochloride (0.115 g, 0.477 mmol) in 6 mL of dichloroethane, triethylamine (0.23 mL, 1.672 mmol) was added, followed by NaBH(OAc)$_3$ (0.118 g, 0.557 mmol). After stirring at room temperature for overnight, the reaction mixture was then quenched with saturated NaHCO$_3$ solution (20 mL) and extracted with ethyl acetate (20 mL×3). The combined organic extracts were dried with anhydrous Na$_2$SO$_4$, filtered, and concentrated under reduced pressure. The resulting residue was purified by column chromatography (silica gel) eluting with 0-10% MeCOH/DCM to give the desired product as a light yellow gum (0.209 g, 99% yield). LC-MS (Method A): $t_R$=4.5 min; (M+H)$^+$: 530.

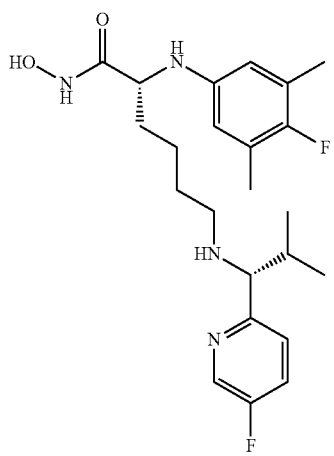 [SMILES: Cc1cc(N[C@H](CCCCN[C@@H](c2ccc(F)cn2)C(C)C)C(=O)NO)cc(C)c1F]

(R)-2-((4-Fluoro-3,5-dimethylphenyl)amino)-6-(((R)-1-(5-fluoropyridin-2-yl)-2-methylpropyl)amino)-N-hydroxyhexanamide (Example Compound 3). To a solution of methyl N2-(4-fluoro-3,5-dimethylphenyl)-N6-((S)-1-(4-fluorophenyl)-2-hydroxyethyl)-N2-(2,2,2-trifluoroacetyl)-D-lysinate (0.209 g, 0.395 mmol) in 4 mL of MeCOH/THF (1:1), a solution of NH$_2$OH in H$_2$O (50%, 1 mL) was added, followed by KCN (0.001 g, 0.0195 mmol). After stirring at room temperature for overnight, the reaction mixture was concentrated under reduced pressure. The resulting residue was purified by column chromatography (amine modified silica gel) eluting with 0-10% MeCOH/DCM to give the desired product as a white solid (0.107 g, 62% yield), LC-MS (Method A): t$_R$=3.5 min; (M+H)$^+$: 435. The product was dissolved in minimum amount of chloroform and HCl in ether (2M) was added. Removal of solvent provided the corresponding HCl salt as a white solid.

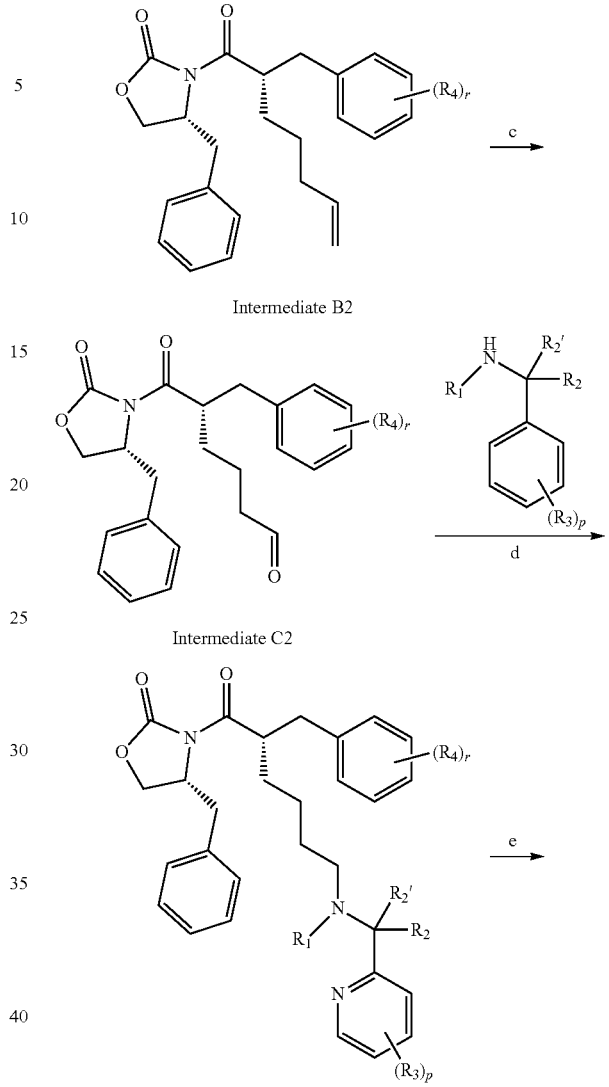

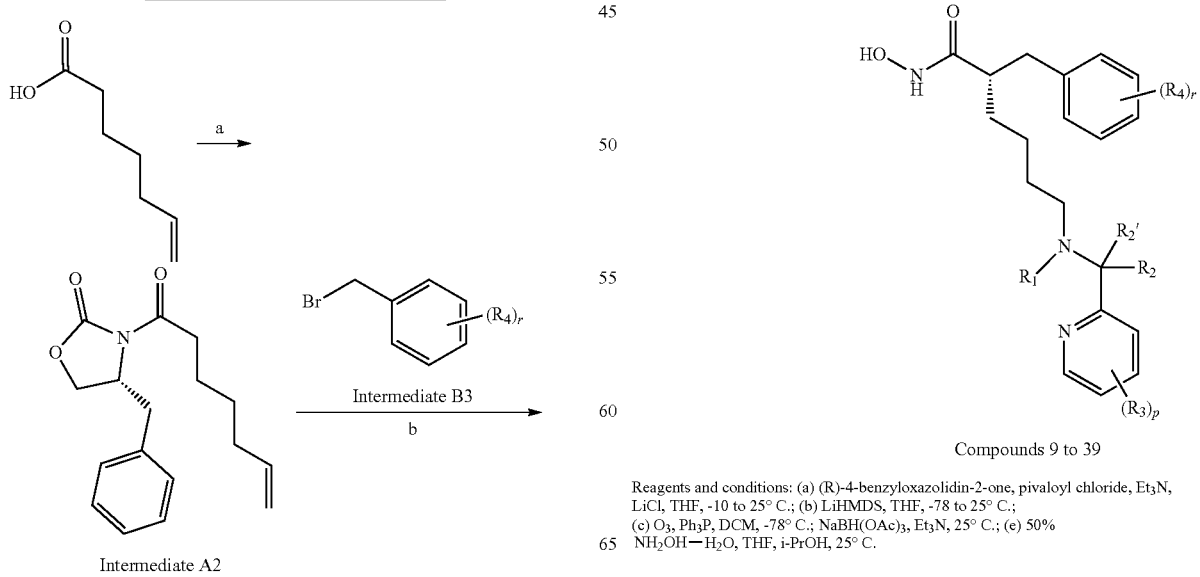

Reagents and conditions: (a) (R)-4-benzyloxazolidin-2-one, pivaloyl chloride, Et$_3$N, LiCl, THF, -10 to 25° C.; (b) LiHMDS, THF, -78 to 25° C.;
(c) O$_3$, Ph$_3$P, DCM, -78° C.; NaBH(OAc)$_3$, Et$_3$N, 25° C.; (e) 50% NH$_2$OH—H$_2$O, THF, i-PrOH, 25° C.

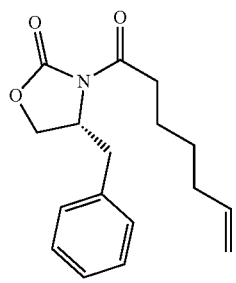 [SMILES: C=CCCCCC(=O)N1C(=O)OC[C@H]1Cc1ccccc1]

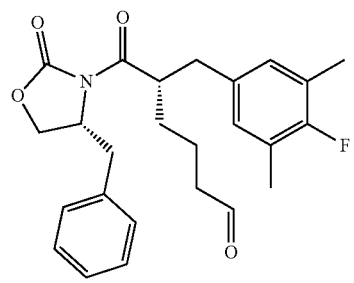

(R)-4-Benzyl-3-(hept-6-enoyl)oxazolidin-2-one (Intermediate A2). To a solution of hept-6-enoic acid (5.000 g, 39.020 mmol) in 100 mL of THF pre-cooled to −10° C., triethylamine (14.7 mL, 105.354 mmol) was added, followed by pivaloyl chloride (5.3 mL, 42.922 mmol). The reaction mixture was stirred at −10° C. under $N_2$ for 1 hour. Then lithium chloride (1.819 g, 42.922 mmol) was added, followed by (R)-4-benzyloxazolidin-2-one (7.606 g, 42.922 mmol). After stirred at −10° C. under $N_2$ for 1 hour, the reaction mixture was warmed to room temperature for overnight. The reaction mixture was then diluted with water (100 mL) and extracted with ethyl acetate (80 mL×3). The combined organic extracts were dried with anhydrous $Na_2SO_4$, filtered, and concentrated under reduced pressure. The resulting residue was purified by column chromatography (silica gel) eluting with 0-50% ethyl acetate/hexanes to give the desired product as a colorless oil (10.980 g, 98% yield). GC-MS (Method C): $t_R$=10.8 min; M$^+$: 287.

(S)-6-((R)-4-Benzyl-2-oxooxazolidin-3-yl)-5-(4-fluoro-3,5-dimethylbenzyl)-6-oxohexanal (Example Intermediate C2). A solution of (R)-4-benzyl-3-((S)-2-(4-fluoro-3,5-dimethylbenzyl)hept-6-enoyl)oxazolidin-2-one (12.660 g, 29.892 mmol) in 150 mL of DCM was cooled to −78° C. The solution was sparged with $O_2$ for 10 minutes, then with $O_3$ until the solution became blue. Then the solution was sparged with $O_2$ again until the solution became clear. Triphenylphosphine (8.232 g, 31.387 mmol) was added. The reaction mixture was warmed to room temperature and stirred for overnight. The solvent was removed and the resulting residue was purified by column chromatography (silica gel) eluting with 0-50% ethyl acetate/hexanes to give the desired product as a colorless oil (11.942 g, 94% yield). GC-MS (Method D): $t_R$=7.2 min; M$^+$: 425.

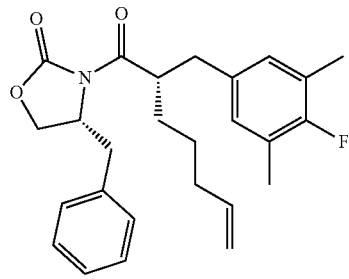 [SMILES: C=CCCC[C@@H](Cc1cc(C)c(F)c(C)c1)C(=O)N1C(=O)OC[C@H]1Cc1ccccc1]

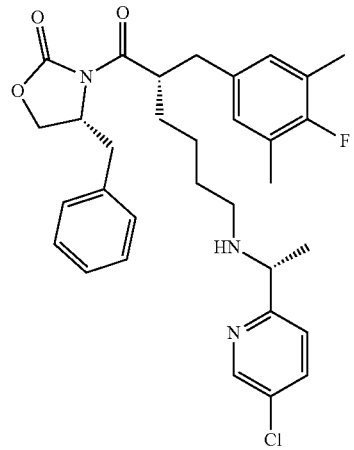 [SMILES: Cc1cc(C[C@H](CCCCN[C@H](C)c2ccc(Cl)cn2)C(=O)N2C(=O)OC[C@H]2Cc2ccccc2)cc(C)c1F]

(R)-4-Benzyl-3-((S)-2-(4-fluoro-3,5-dimethylbenzyl)hept-6-enoyl)oxazolidin-2-one (Example Intermediate B2). To a solution of (R)-4-benzyl-3-(hept-6-enoyl)oxazolidin-2-one (10.800 g, 37.584 mmol) in 80 mL of THF pre-cooled to −78° C., LiHMDS (1 M in THF, 45.1 mL, 45.101 mmol) was added. The reaction mixture was stirred at −78° C. under $N_2$ for 1 hour. Then a solution of 5-(bromomethyl)-2-fluoro-1,3-dimethylbenzene (10.606 g, 48.859 mmol) in 20 mL of THF was added. After stirred at −78° C. under $N_2$ for 1 hour, the reaction mixture was warmed to room temperature for 2 hours. The reaction mixture was then quenched with saturated $NH_4Cl$ solution (100 mL) and extracted with ethyl acetate (80 mL×3). The combined organic extracts were dried with anhydrous $Na_2SO_4$, filtered, and concentrated under reduced pressure. The resulting residue was purified by column chromatography (silica gel) eluting with 0-30% ethyl acetate/hexanes to give the desired product as a light yellow oil (13.316 g, 84% yield). GC-MS (Method D): $t_R$=6.7 min; M$^+$: 423.

(R)-4-Benzyl-3-((S)-6-(((R)-1-(5-chloropyridin-2-yl)ethyl)amino)-2-(4-fluoro-3,5-dimethylbenzyl)hexanoyl)oxazolidin-2-one (Example Intermediate D2). To a mixture of (S)-6-((R)-4-benzyl-2-oxooxazolidin-3-yl)-5-(4-fluoro-3,5-dimethylbenzyl)-6-oxohexanal (8.680 g, 20.400 mmol) and (R)-1-(5-chloropyridin-2-yl)ethan-1-amine hydrochloride (5.619 g, 24.480 mmol) in 200 mL of dichloroethane, triethylamine (11.9 mL, 85.580 mmol) was added, followed by NaBH(OAc)$_3$ (6.053 g, 28.560 mmol). After stirring at room temperature for overnight, the reaction mixture was quenched with saturated NaHCO$_3$ solution (150 mL) and extracted with ethyl acetate (150 mL×3). The combined organic extracts were dried with anhydrous $Na_2SO_4$, filtered, and concentrated under reduced pressure. The resulting residue was purified by column chromatography (silica gel) eluting with 0-15% EtOH/DCM to give the desired product as a yellow gum (10.810 g, 94% yield). LC-MS (Method A): $t_R$=5.1 min; (M+H)$^+$: 566.

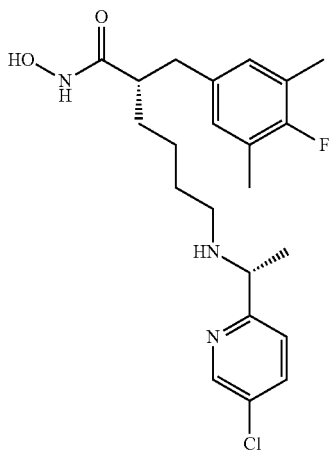 [SMILES: Cc1cc(C[C@H](CCCCN[C@H](C)c2ccc(Cl)cn2)C(=O)NO)cc(C)c1F]

(S)-6-(((R)-1-(5-Chloropyridin-2-yl)ethyl)amino)-2-(4-fluoro-3,5-dimethylbenzyl)-N-hydroxyhexanamide (Example Compound 27). To a solution of (R)-4-benzyl-3-((S)-6-(((R)-1-(5-chloropyridin-2-yl)ethyl)amino)-2-(4-fluoro-3,5-dimethylbenzyl)hexanoyl)oxazolidin-2-one (10.310 g, 18.212 mmol) in 200 mL of i-PrOH/THF (1:1), a solution of NH$_2$OH in H$_2$O (50%, 50 mL) was added. After stirring at room temperature for overnight, the reaction mixture was concentrated under reduced pressure. The resulting residue was purified by column chromatography (amine modified silica gel) eluting with 0-15% EtOH/DCM to give the desired product as a white solid (6.200 g, 81% yield). LC-MS (Method A): $t_R$=4.0 min; (M+H)$^+$: 422. The product was dissolved in minimum amount of chloroform and HCl in ether (2M) was added. Removal of solvent provided the corresponding HCl salt as a white solid.

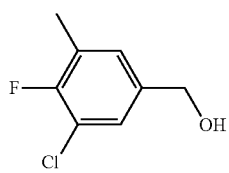

(3-Chloro-4-fluoro-5-methylphenyl)methanol (Example Intermediate A3). To a solution of 3-chloro-4-fluoro-5-methylbenzoic acid (4.000 g, 21.211 mmol) in 80 mL of THF pre-cooled to 0° C., a solution of LAH in Et$_2$O (1 M, 35.9 mL, 35.900 mmol) was added. After being stirred at 0° C. for 1 hour then 25° C. for overnight under N$_2$, the reaction mixture was quenched 1 N HCl at 0° C. and extracted with ethyl acetate (80 mL×3). The combined organic extracts were dried with anhydrous Na$_2$SO$_4$, filtered, and concentrated under reduced pressure. The resulting residue was purified by column chromatography (silica gel) eluting with 0-50% ethyl acetate/hexanes to give the desired product as a colorless oil (3.408 g, 92% yield). GC-MS (Method E): $t_R$=6.9 min; M$^+$: 174.

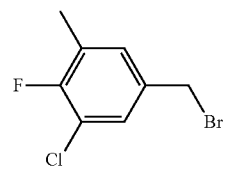

5-(Bromomethyl)-1-chloro-2-fluoro-3-methylbenzene (Example Intermediate B3). To a solution of (3-chloro-4-fluoro-5-methylphenyl)methanol (3.408 g, 19.519 mmol) and CBr$_4$ (6.473 g, 19.519 mmol) in 100 mL of DCM pre-cooled to 0° C., Ph$_3$P (5.120 g, 19.519 mmol) was added. After being stirred at 0° C. under N$_2$ for 3 hours, the reaction mixture was concentrated under reduced pressure. The resulting residue was purified by column chromatography (silica gel) eluting with 0-15% ethyl acetate/hexanes to give the desired product as a light yellow oil (3.159 g, 68% yield). GC-MS (Method E): $t_R$=7.0 min; M$^+$: 236.

Scheme 3 Synthesis of benxyl bromides

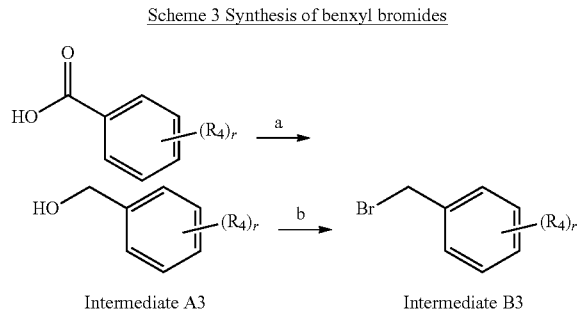

Intermediate A3 → Intermediate B3
Reagents and conditions: (a) LAH, THF, 0 to 25° C.; (b) Ph$_3$P, CBr$_4$, DCM, 0° C.

Scheme 4 Synthesis of intermediate K4

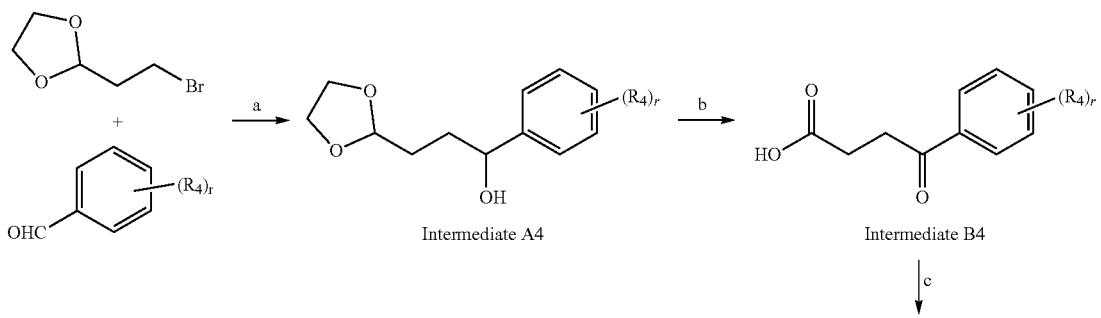

Intermediate A4 → Intermediate B4

-continued

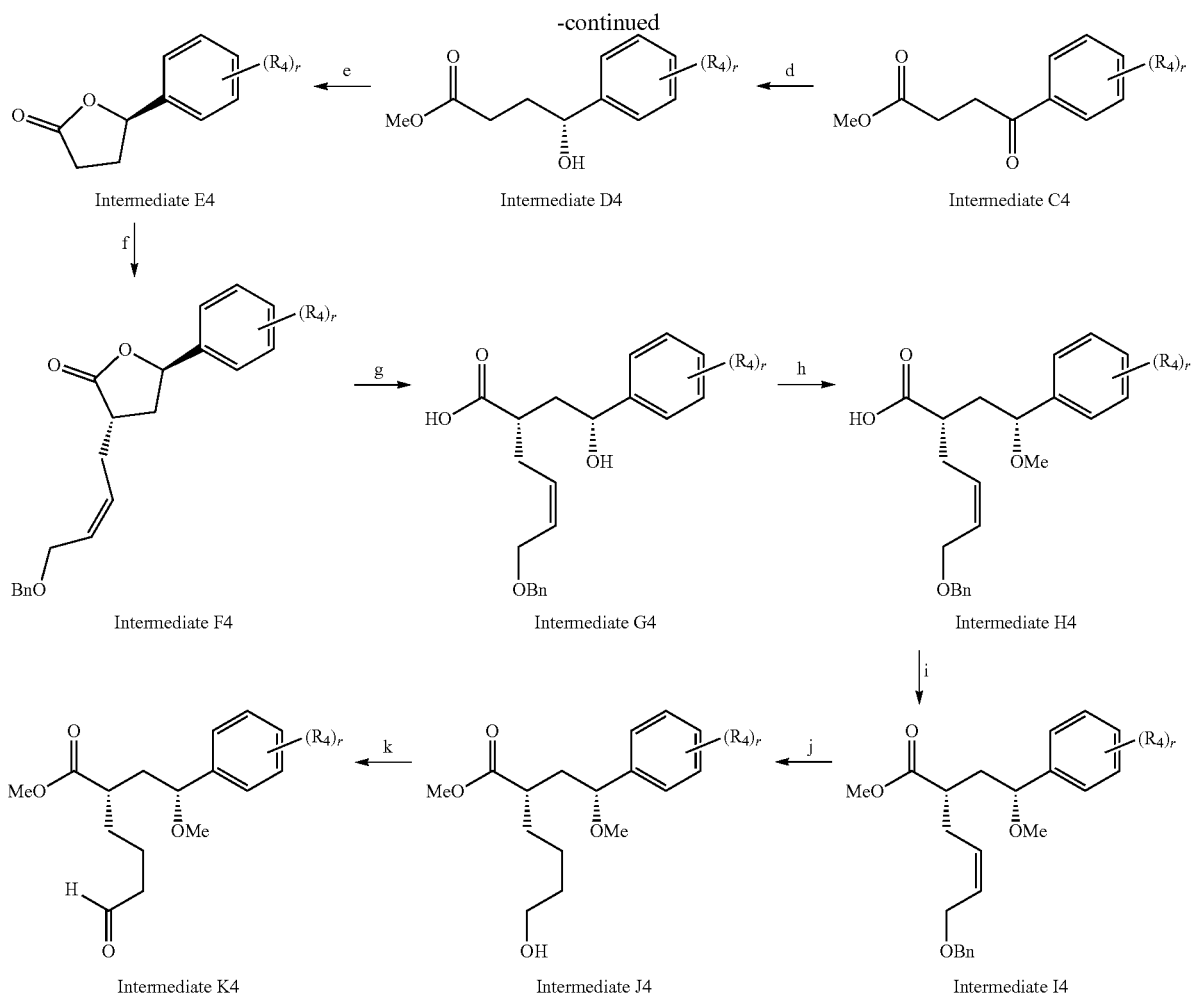

Reagents and conditions: a) Mg, I₂, THF, -78 to 25° C., 3 h; b) Jones Oxidation, acetone, 60° C., 30 min; c) H⁺, MeOH, 25° C., 8 h; d) (S)-2-methyl-CBS-oxazaborolidine, BH₃, THF, 25° C., 1 h; e) TFA, DCM, 42° C., 8 h; f) LiHMDS, (Z)-(((4-bromobut-2-en-1-yl)oxy)methyl)benzene, -78° to 20° C., 8 h; g) KOH, H₂O, dioxane, 25° C., 30 min; h) MeI, NaH, DMF, 0 to 25° C., 3 h; i) TMSCHN₂, DCM, MeOH, 25° C., 30 min; j) H₂, Pd/C, EtOH, 25° C., 3 h; k) DMP, DCM, 25° C., 3 h

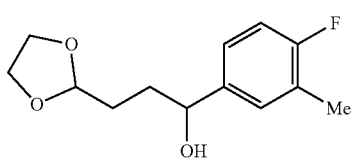 [SMILES: Cc1cc(C(O)CCC2OCCO2)ccc1F]

3-(1,3-Dioxolan-2-yl)-1-(4-fluoro-3-methyl phenyl)propan-1-ol (Example Intermediate A4): To a suspension of Mg turnings (709 mg, 29.2 mmol) and catalytic amount of iodine in 80 mL THF was added dropwise 2-(2-bromoethyl)-1,3-dioxolane (264.3 mg, 14.6 mmol) with heating over a period of 30 min. After stirring for an additional 30 min at 25° C., the mixture was cooled to −78° C. and 4-fluoro-3-methylbenzaldehyde (2.0 g, 14.5 mmol) was added slowly as a solution in 5 mL THF. The temperature was maintained at −78 to −30° C. for 1 h and slowly raised to room temperature. The excess Grignard reagent was destroyed by careful addition of saturated aqueous NH₄Cl (40 mL). The mixture was extracted with ethyl acetate (3×40 mL) and the combined organic layers were washed with brine (2×30 mL) and dried over Na₂SO₄. After removal of the solvent under reduced pressure the product was isolated by flash column chromatography (silica gel) to afford 2.7 g of the title compound as a light yellow oil. LC/MS (Method A): $t_R$=5.2 min. MS (API-ES) m/z 463 (M+Na⁺)

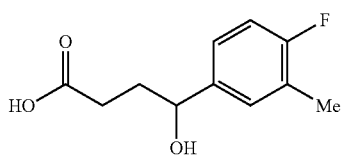 [SMILES: Cc1cc(C(O)CCC(=O)O)ccc1F]

4-(4-Fluoro-3-methylphenyl)-4-oxobutanoic acid (Example Intermediate B4): 3-(1,3-dioxolan-2-yl)-1-(4-fluoro-3-methylphenyl)propan-1-ol (2.0 g, 8.3 mmol) in 30 mL acetone was added 16 mL of Jones reagent dropwise at 60° C. After stirring an additional 30 min, 40 mL water was added and the mixture extracted with DCM (3×40 mL). The combined DCM layers were washed with brine (2×30 mL) and dried over Na₂SO₄. The solvent was evaporated under reduce pressure and the crude product was used for the next step without further purification. LC/MS (Method A): $t_R$=5.7 min. MS (API-ES) m/z 233 (M+Na$^+$)

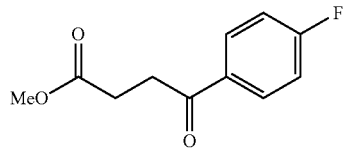 [SMILES: COC(=O)CCC(=O)c1ccc(F)cc1]

Methyl 4-(4-fluorophenyl)-4-oxobutanoate (Example Intermediate C4): To a solution of 4-(4-fluoro-3-methyl-phenyl)-4-oxo-butyric acid (3.0 g, 15.3 mmol) in 30 mL methanol was added 1.0 mL concentrated H$_2$SO$_4$ and the mixture was stirred for 16 h at 25° C. The mixture was concentrated under reduced pressure, 30 mL water was added, and the resulting mixture extracted with ethyl acetate (3×50 mL). The combined organic layers were washed with brine (2×20 mL) and dried over Na$_2$SO$_4$. Evaporation of the solvent gave the desired methyl ester (3.2 g) as light yellow solid which was used without further purification in the next reaction. LC/MS (Method A): $t_R$=6.9 min. MS (API-ES) m/z 211 (M+H$^+$)

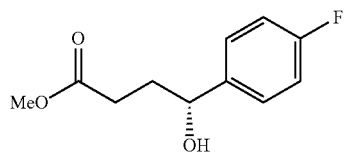 [SMILES: COC(=O)CC[C@@H](O)c1ccc(F)cc1]

Methyl (R)-4-(4-fluorophenyl)-4-hydroxybutanoate (Example Intermediate D4): To a solution of BH$_3$.THF (1 M, 5.7 mL, 5.7 mmol) in 40 mL anhydrous THF was dropwise added at room temperature (S)-2-methyl-CBS-oxazaborolidine (952 µL, 0.952 mmol, 1 M in toluene). After stirring for 5 minutes, methyl 4-(4-fluorophenyl)-4-oxobutanoate (2.0 g, 9.5 mmol) was added as a solution in 25 mL THF. The reaction mixture was stirred for 30 min at room temperature and then quenched by the slow addition of saturated aqueous ammonium chloride (60 mL). The resulting mixture was extracted with ethyl acetate (3×50 mL) and the combined organic layers washed with brine (2×40 mL) and dried over Na$_2$SO$_4$. The solvent was evaporated under reduced pressure and the product isolated by silica gel Flash chromatography to afford 1.7 g of the title compound as a colorless oil. LC/MS (Method A): $t_R$=5.7 min. MS (API-ES) m/z 235 (M+H$^+$+Na$^+$). Optical purity; 95% ee determined by $^1$H-NMR analysis of the Mosher esters.

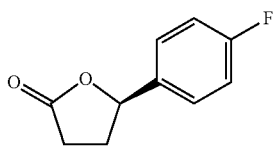 [SMILES: O=C1CC[C@H](c2ccc(F)cc2)O1]

(R)-5-(4-Fluorophenyl)dihydrofuran-2(3H)-one (Example Intermediate E4): To a solution of (R)-methyl 4-(4-fluorophenyl)-4-hydroxybutanoate (1.7 g, 8.0 mmol) in DCM (40 mL) was added 8 drops TFA at room temperature. The reaction mixture was warmed to 40° C. and stirred for 16 h. Evaporation of the solvent gave a light yellow oil from which the product was isolated by Flash chromatography (silica gel) eluting with 0% to 30% ethyl acetate/hexane to give 1.6 g of the title compound as a colorless oil. LC/MS (Method A): $t_R$=6.2 min. MS (API-ES) m/z 181 (M+H$^+$)

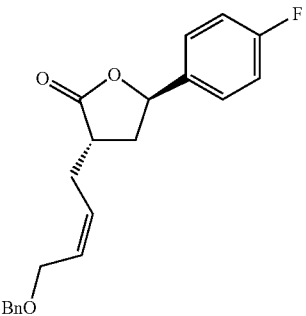 [SMILES: O=C1O[C@@H](c2ccc(F)cc2)C[C@@H]1C/C=C\COCc1ccccc1]

(3S,5R)-3-((Z)-4-(Benzyloxy)but-2-en-1-yl)-5-(4-fluorophenyl)dihydrofuran-2(3H)-one (Example Intermediate F4): To a solution of lithium bis(trimethylsilyl)amide (4.6 mL, 4.6 mmol, 1 M in THF) in anhydrous 40 mL THF at −70° C. was slowly added over 15 minutes ((R)-5-(4-fluorophenyl)dihydrofuran-2(3H)-one (685 mg, 3.8 mmol) as a solution in 4 mL THF. After the reaction mixture was stirred for 30 min at −70° C. a pre-cooled solution of (4-Iodo-but-2-enyloxymethyl)-benzene (1.3 g, 4.6 mmol) in 4 mL of THF was slowly added. The resulting mixture was stirred at −70° C. for 1 h and the temperature was slowly raised to room temperature over a period of 2 h. The mixture was poured into 20 mL saturated NH$_4$Cl and extracted with ethyl acetate (3×50 mL). The combined organic layers were washed with brine (2×30 mL) and dried over Na$_2$SO$_4$. The solvent was removed under reduced pressure and the product isolated by Flash column chromatography (silica gel) eluting with 0% to 50% ethyl acetate/hexane to give 827 mg of the title compound as a light yellow oil. GCMS (Method F) (EI) m/z 139 (M-201) base peak.

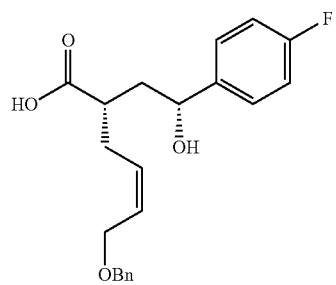 [SMILES: O=C(O)[C@@H](C/C=C\COCc1ccccc1)C[C@@H](O)c1ccc(F)cc1]

(S,Z)-6-(Benzyloxy)-2-((R)-2-(4-fluorophenyl)-2-hydroxyethyl)hex-4-enoic acid (Example Intermediate G4): To a solution of (3S,5R)-3-(4-(benzyloxy)but-2-enyl)-5-(4-fluorophenyl)dihydrofuran-2(3H)-one (643 mg, 1.9 mmol) in 7 mL dioxane was added 7 mL aqueous 5% KOH at 25° C. After being stirred for 30 min at room temperature the reaction was quenched by the addition of 10 mL of 1 M aqueous HCl. The mixture was extracted ethyl acetate (2×50 mL) and the combined organic layers were washed with brine (2×30 mL). The solution was dried over Na$_2$SO$_4$ before being concentrated under reduced pressure. The crude product was used directly in the next reaction without further purification. GCMS (Method F) (EI) m/z 139 (M-219) base peak.

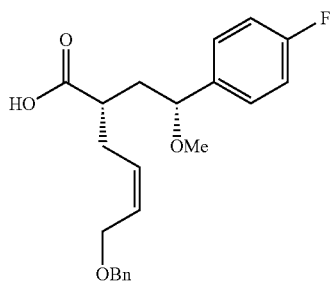 [SMILES: CO[C@H](C[C@H](C/C=C\COCc1ccccc1)C(=O)O)c1ccc(F)cc1]

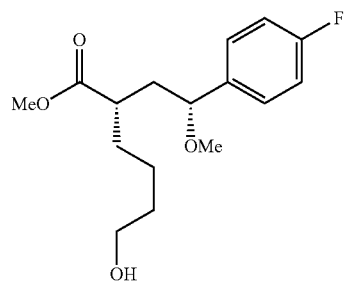

(S,Z)-6-(Benzyloxy)-2-((R)-2-(4-fluorophenyl)-2-methoxyethyl)hex-4-enoic acid (Example Intermediate H4): To a suspension of NaH (605 mg, 60% oil dispersion) in 30 mL THF was slowly added at room temperature the crude (S)-6-(benzyloxy)-2-((R)-2-(4-fluorophenyl)-2-hydroxyethyl)hex-4-enoic acid isolated above as a solution in 5 mL THF. To this mixture was added dropwise methyl iodide (732 µL, 1.7 g, 11.3 mmol) and the resulting stirred for 3 h at room temperature. The reaction was quenched by the slow addition of 20 mL 1 M aqueous HCl and the mixture extracted with ethyl acetate (3×50 mL). The combined organic layers were washed with brine (2×30 mL) and dried over sodium sulfate. Evaporation of solvent afforded the product as an oil which was used directly in the next reaction without further purification. GCMS (Method F) (EI) m/z 91 (M-281) base peak.

Methyl (S)-2-((R)-2-(4-fluorophenyl)-2-methoxyethyl)-6-hydroxyhexanoate (Example Intermediate J4): (S)-methyl 6-(benzyloxy)-2-((R)-2-(4-fluorophenyl)-2-methoxyethyl)hex-4-enoate (494 mg, 1.2 mmol) was dissolved into 5 mL EtOH and to it added 10% Pd/C (450 mg). The solution was saturated with $H_2$ (stream of $H_2$ bubbled through solution) and then stirred for 3 h at room temperature under one atmosphere of hydrogen (balloon). The mixture was filtered through a bed of Celite and rinsed with ethyl acetate. The solvent was removed under reduced pressure and the crude product used directly in the next step without further purification. GCMS (Method F) (EI) m/z 91 (M-207) base peak.

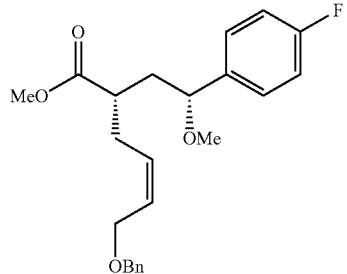 [SMILES: COC(=O)[C@@H](C/C=C\COCc1ccccc1)C[C@@H](OC)c1ccc(F)cc1]

Methyl (S,Z)-6-(benzyloxy)-2-((R)-2-(4-fluorophenyl)-2-methoxyethyl)hex-4-enoate (Example Intermediate 14): To a solution of ((S)-6-(benzyloxy)-2-((R)-2-(4-fluorophenyl)-2-methoxyethyl)hex-4-enoic acid in 10 mL methanol was added concentrated $H_2SO_4$ (150 µL) at room temperature and the resulting solution stirred for 8 h. The reaction mixture was concentrated under reduced pressure, the residue treated with water, and the mixture was extracted with ethyl acetate (3×40 mL). The combined organic layers were washed with brine (2×30 mL) and dried over $Na_2SO_4$. The product was isolated by flash column chromatography (silica gel) eluting with 0% to 20% ethyl acetate/hexane gradient solvent to give 494 mg of the title compound as a colorless oil. GCMS (Method F) (EI) m/z 91 (M-295) base peak.

Methyl (S)-2-((R)-2-(4-fluorophenyl)-2-methoxyethyl)-6-oxohexanoate (Example Intermediate K4): To the crude solution of ((S)-methyl 2-((R)-2-(4-fluorophenyl)-2-methoxyethyl)-6-hydroxyhexanoate isolated above (100 mg, 0.33 mmol) in 10 mL DCM was added Dess-Martin periodinane (284 mg, 0.67 mmol) at 25° C. After being stirred for 3 h at 25° C., the mixture was filtered through a bed of Celite and rinsed with more DCM. The solvent was removed under reduced pressure and the product isolated by Flash column chromatography (silica gel) eluting with 0% to 50% ethyl acetate/hexane to give 78 mg of the title compound as a light yellow oil. GCMS (Method F) (EI) m/z 91 (M-205) base peak.

Scheme 5 Synthesis of compounds 39-58
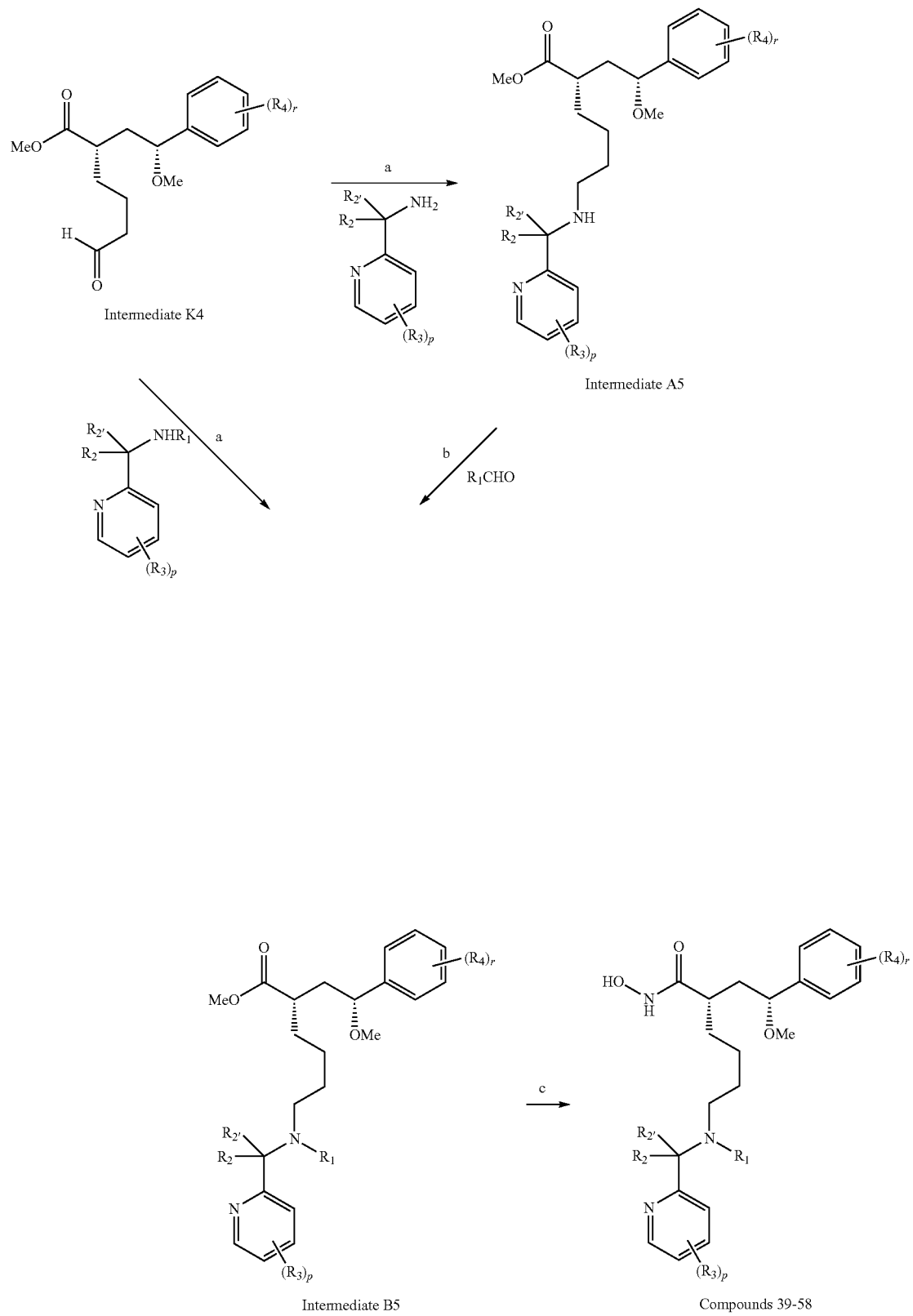
Reagents and conditions: a) NaBH(OAc)₃, Et₃N, MeOH, 25° C., 8 h; b) NaBH(OAc)₃, AcOH, DCE, 25° C., 8 h; c) NH₂OH, KCN, MeOH, THF, H₂O, 25° C., 24 h.

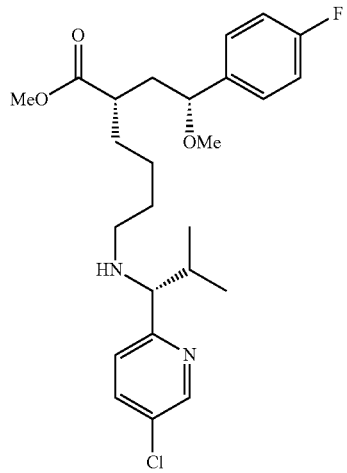 [SMILES: COC(=O)[C@@H](CCCCN[C@@H](c1ccc(Cl)cn1)C(C)C)C[C@@H](OC)c1ccc(F)cc1]

Methyl (S)-6-(((R)-1-(5-chloropyridin-2-yl)-2-methylpropyl)amino)-2-((R)-2-(4-fluorophenyl)-2-methoxyethyl)hexanoate (Example Intermediate A5): To a solution of (S)-methyl 2-((R)-2-(4-fluorophenyl)-2-methoxyethyl)-6-oxohexanoate (Example Intermediate K4) (150 mg, 0.5 mmol) in 2 mL MeCOH was added (R)-1-(5-chloropyridin-2-yl)-2-methylpropan-1-amine hydrochloride (307 mg, 1.2 mmol) and Et$_3$N (276 μL, 2.0 mmol) followed by NaBH(OAc)$_3$ (296 mg, 1.4 mmol) at room temperature. The mixture was stirred for 8 h at the room temperature. The reaction was quenched by pouring into 20 mL 5% aqueous NaOH and diluted with ethyl acetate. The mixture was extracted with more ethyl acetate (3×30 mL) and the combined organic layers washed with brine (2×20 mL) and dried over Na$_2$SO$_4$. The solvent was removed under reduced pressure and the product isolated by Flash column chromatography (silica gel) eluting with 0% to 30% ethyl acetate/hexane and 0% to 15% MeCOH/DCM to give 320 mg of the title compound as a light yellow oil. LC/MS (Method A): t$_R$=4.5 min. MS (API-ES) m/z 466 (M+H$^+$).

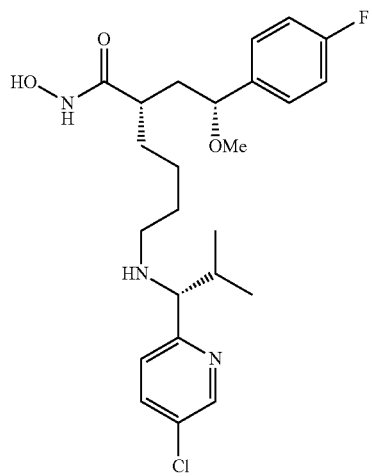 [SMILES: CO[C@H](C[C@H](CCCCN[C@@H](c1ccc(Cl)cn1)C(C)C)C(=O)NO)c1ccc(F)cc1]

(S)-6-(((R)-1-(5-chloropyridin-2-yl)-2-methylpropyl)amino)-2-((R)-2-(4-fluorophenyl)-2-methoxyethyl)-N-hydroxyhexanamide (Example Compound 51): To a solution of methyl (S)-6-(((R)-1-(5-chloropyridin-2-yl)-2-methylpropyl)amino)-2-((R)-2-(4-fluorophenyl)-2-methoxyethyl) hexanoate dissolved in 5 mL of THF, methanol, and 50 wt % NH$_2$OH in H$_2$O (2:2:1) was added KCN (10.0 mg). The resulting mixture stirred for one days at room temperature. Evaporation of solvent left the crude from which the product was isolated by column chromatography (amine modified silica gel) eluting with 0% to 25% EtOH/DCM to give the title compound, 35 mg, as light brown oil. LC/MS (Method A): t$_R$=3.3 min. MS (API-ES) m/z 466 (M+H$^+$)

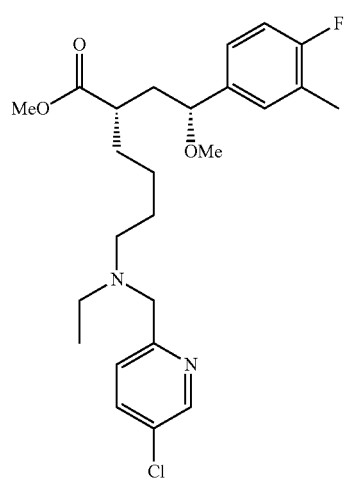 [SMILES: CCN(CCCC[C@@H](C[C@@H](OC)c1ccc(F)c(C)c1)C(=O)OC)Cc1ccc(Cl)cn1]

Methyl (S)-6-(((5-chloropyridin-2-yl)methyl)(ethyl)amino)-2-((R)-2-(4-fluoro-3-methylphenyl)-2-methoxyethyl)hexanoate (Example Intermediate B5): To a solution of methyl (S)-6-(ethylamino)-2-((R)-2-(4-fluorophenyl)-2-methoxyethyl)hexanoate (87 mg, 0.26 mmol) in 5 mL DCE was added 5-chloropicolinaldehyde (51 mg, 0.35 mmol) followed by NaBH(OAc)$_3$ (73 mg, 0.35 mmol) and AcOH (18.7 mg, 1.2 mmol) at room temperature. The mixture was stirred for 8 h at the room temperature. The reaction was quenched by pouring into 10 mL 5% aqueous NaOH and diluted with ethyl acetate. The mixture was extracted with more ethyl acetate (3×20 mL) and the combined organic layers washed with brine (2×20 mL) and dried over Na$_2$SO$_4$. The solvent was removed under reduced pressure and the product isolated by Flash column chromatography (silica gel) eluting with 0% to 30% ethyl acetate/hexane and 0% to 15% MeCOH/DCM to give 89 mg of the title compound as a light yellow oil. LC/MS (Method A): t$_R$=4.4 min. MS (API-ES) m/z 465 (M+H$^+$)

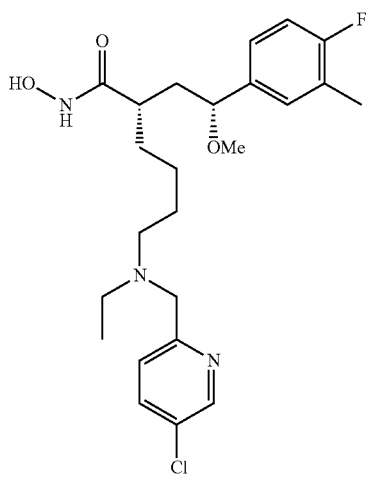 [SMILES: CCN(CCCC[C@@H](C[C@@H](OC)c1ccc(F)c(C)c1)C(=O)NO)Cc1ccc(Cl)cn1]

(S)-6-(((5-chloropyridin-2-yl)methyl)(ethyl)amino)-2-((R)-2-(4-fluoro-3-methylphenyl)-2-methoxyethyl)-N-hydroxyhexanamide (Example Compound 57): To a solution of methyl (S)-6-(((5-chloropyridin-2-yl)methyl)(ethyl)amino)-2-((R)-2-(4-fluoro-3-methylphenyl)-2-methoxyethyl)hexanoate (89 mg, 0.19 mmol) dissolved in 5 mL of THF, methanol, and 50 wt % $NH_2OH$ in $H_2O$ (2:2:1) was added KCN (10.0 mg). The resulting mixture stirred for one day at room temperature. Evaporation of solvent left the crude from which the product was isolated by column chromatography (amine modified silica gel) eluting with 0% to 25% EtOH/DCM to give the title compound, 25 mg, as light brown oil. LC/MS (Method A): $t_R$=3.5 min. MS (API-ES) m/z 466 (M+H$^+$).

Analytical Methods: LCMS conditions-LCMS spectra were recorded on a Shimadzu LCMS-2020 DUIS with Nexera PDA and Sedex ELSD detectors and DUIS Electrospray (ESI+/−) ionization. The methods used were: (A) a solvent gradient beginning with 80% mobile phase A (mobile phase A=0.1% formic Acid in $H_2O$) and ending with 98% B (mobile phase B=0.1% formic Acid in MeCN) at a flow rate of 1.0 mL/min with a run time of 11.0 minutes using a Zorbax XDB C18 (3.5 μm) column (4.6×75 mm); or (B) a solvent gradient beginning with 95% mobile phase A (mobile phase A=0.1% formic Acid in $H_2O$) and ending with 95% B (mobile phase B=0.1% formic Acid in MeCN) at a flow rate of 1.0 mL/min with a run time of 11.0 minutes using a Zorbax XDB C18 (3.5 μm) column (4.6×75 mm).

GCMS conditions-GCMS was performed with a Shimadzu GC-2010 gas chromatography instrument coupled to a Shimadzu GCMS-QP2010S mass spectrometer and a GCMS Solution software Ver. 2.70 (Shimadzu). The methods used were; (C) a SH-Rxi-5Sil MS column (30 m×0.25 mm i.d.) coated with 0.25 μm film 5% diphenyl/95% dimethylpolysiloxane was used for separation. Ultra High purity helium was used as carrier gas with flow-rate at 1.46 mL/min. The spectrometer was operated in electron-impact (EI) mode, the scan range was 40-600 amu, the ionization energy was 70 eV, and the scan rate was 0.5 s per scan. The ionization source temperature was 200° C. For each sample analysis, 3 μL was injected in split mode with a Split ratio 15. The GC oven was initially heated isothermally at 70° C. held for 0.5 min, then increased to 300° C. (20° C./min) and held for 3 min at this final temperature; (D) a SH-Rxi-5Sil MS column (30 m×0.25 mm i.d.) coated with 0.25 μm film 5% diphenyl/95% dimethylpolysiloxane was used for separation. Ultra High purity helium was used as carrier gas with flow-rate at 1.35 mL/min. The spectrometer was operated in electron-impact (EI) mode, the scan range was 40-600 amu, the ionization energy was 70 eV, and the scan rate was 0.5 s per scan. The ionization source temperature was 200° C. For each sample analysis, 3 μL was injected in split mode with a Split ratio 20. The GC oven was initially heated isothermally at 200° C. held for 0.5 min, then increased to 330° C. (20° C./min) and held for 3 min at this final temperature; (E) a SH-Rxi-5Sil MS column (30 m×0.25 mm i.d.) coated with 0.25 μm film 5% diphenyl/95% dimethylpolysiloxane was used for separation. Ultra High purity helium was used as carrier gas with flow-rate at 1.51 mL/min. The spectrometer was operated in electron-impact (EI) mode, the scan range was 40-600 amu, the ionization energy was 70 eV, and the scan rate was 0.5 s per scan. The ionization source temperature was 200° C. For each sample analysis, 3 μL was injected in split mode with a Split ratio 15. The GC oven was initially heated isothermally at 40° C. held for 0.5 min, then increased to 300° C. (20° C./min) and held for 3 min at this final temperature; or (F) a SH-Rxi-5Sil MS column (30 m×0.25 mm i.d.) coated with 0.25 μm film 5% diphenyl/95% dimethylpolysiloxane was used for separation. Ultra High purity helium was used as carrier gas with flow-rate at 1.46 mL/min. The spectrometer was operated in electron-impact (EI) mode, the scan range was 40-600 amu, the ionization energy was 70 eV, and the scan rate was 0.35 s per scan. The ionization source temperature was 200° C. For each sample analysis, 3 μL was injected in split mode with a Split ratio 4.0. The GC oven was initially heated isothermally at 100° C. held for 1 min, then increased to 320° C. (35° C./min) and held for 10 min at this final temperature.

Table 1 below summarizes the abbreviations used in conjunction with Synthetic Schemes 1-5 above.

TABLE 1

| | |
|---|---|
| DMF | dimethylformamide |
| DCM | dichloromethane |
| DCE | 1,2-dichloroethane |
| DMSO | dimethyl sulfoxide |
| DMPAO | 2-(2,6-dimethylphenylamino)-2-oxoacetic acid |
| pyBOP | benzotriazol-1-yl-oxy-tris-pyrrolidino-phosphonium hexafluorophosphate |
| EtOAc | ethyl acetate |
| THF | tetrahydrofuran |
| DIEA | N,N-diisopropylethylamine |
| Jones oxidation reagent | $H_2CrO_4/H_2SO_4/H_2O$ |
| DMP | Dess-Martin periodinane |
| n-BuLi | n-Butyllithium |
| MeOH | methanol |
| LAH | lithium aluminum hydride |
| TMS | trimethylsilyl |
| Xc | chiral auxiliary |
| Ipc | isopinocampheyl |
| HMDS | hexamethyldisilazide |
| IR | infared spectroscopy |
| MS(EI) | mass spectrometry(electron impact) |
| OEt | ethoxy (—$OCH_2CH_3$) |
| OMe | methoxy (—$OCH_3$) |
| OAc | acetate (OC(O)$CH_3$) |
| $Ph_3P$ or $PPh_3$ | triphenylphosphine |
| EtOH | ethanol |
| $Et_2O$ | diethyl ether |
| MS(API-ES) | mass spectrometry(atmospheric pressure ionization-electrospray) |

Characterizing data for Exemplary Compounds

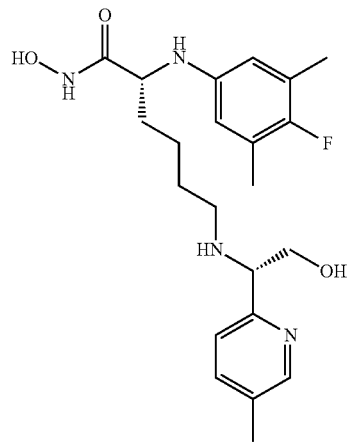 [SMILES: Cc1ccc([C@@H](CO)NCCCC[C@@H](Nc2cc(C)c(F)c(C)c2)C(=O)NO)nc1]

Name: (R)-2-((4-fluoro-3,5-dimethylphenyl)amino)-N-hydroxy-6-(((S)-2-hydroxy-1-(5-methylpyridin-2-yl)ethyl)amino)hexanamide
Compound: 1
LC/MS (Method A): $t_R$ = 3.9 min, $(M + H)^+$ = 419
IR: 3329.25, 2926.11, 1652.09, 1494.88, 1216.16, 1035.81, 756.12 $cm^{-1}$

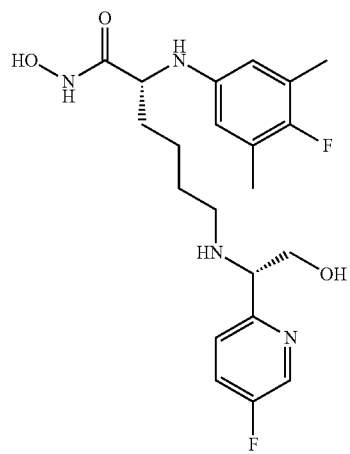 [SMILES: Cc1cc(N[C@H](CCCCN[C@H](CO)c2ccc(F)cn2)C(=O)NO)cc(C)c1F]

Name: (R)-2-((4-fluoro-3,5-dimethylphenyl)amino)-6-(((S)-1-(5-fluoropyridin-2-yl)-2-hydroxyethyl)amino)-N-hydroxyhexanamide
Compound: 2
LC/MS (Method A): $t_R$ = 3.9 min, $(M + H)^+$ = 423
IR: 3319.60, 2925.15, 1653.05, 1486.20, 1217.12, 1068.60, 757.09 $cm^{-1}$

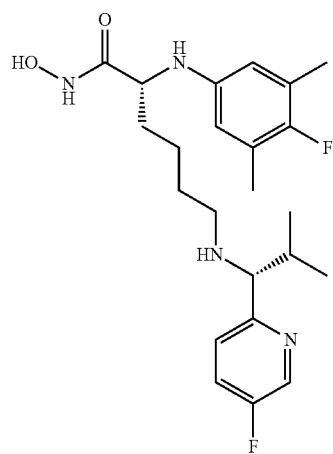 [SMILES: Cc1cc(N[C@H](CCCCN[C@@H](c2ccc(F)cn2)C(C)C)C(=O)NO)cc(C)c1F]

Name: (R)-2-((4-fluoro-3,5-dimethylphenyl)amino)-6-(((R)-1-(5-fluoropyridin-2-yl)-2-methylpropyl)amino)-N-hydroxyhexanamide
Compound: 3
LC/MS (Method A): $t_R$ = 3.5 min, $(M + H)^+$ = 435
IR: 3202.91, 2926.11, 1652.09, 1505.49, 1217.12, 1022.31, 847.74, 738.76 $cm^{-1}$

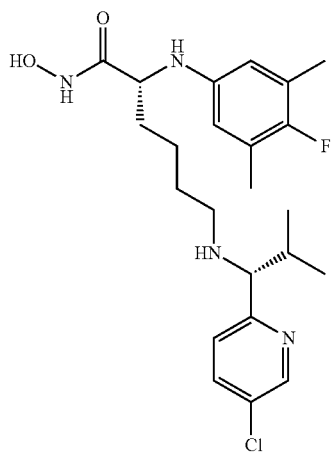 [SMILES: Cc1cc(N[C@H](CCCCN[C@@H](c2ccc(Cl)cn2)C(C)C)C(=O)NO)cc(C)c1F]

Name: (R)-6-(((R)-1-(5-chloropyridin-2-yl)-2-methylpropyl)amino)-2-((4-fluoro-3,5-dimethylphenyl)amino)-N-hydroxyhexanamide
Compound: 4
LC/MS (Method A): $t_R$ = 3.7 min, $(M + H)^+$ = 451
IR: 3197.12, 2926.11, 1652.09, 1494.88, 1215.19, 1110.07, 844.85, 738.76 $cm^{-1}$

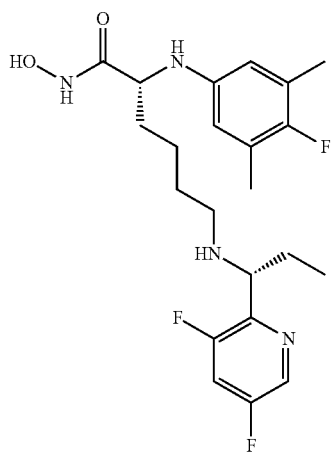 [SMILES: CC[C@@H](NCCCC[C@@H](Nc1cc(C)c(F)c(C)c1)C(=O)NO)c1ncc(F)cc1F]

Name: (R)-6-(((R)-1-(3,5-difluoropyridin-2-yl)propyl)amino)-2-((4-fluoro-3,5-dimethylphenyl)amino)-N-hydroxyhexanamide
Compound: 5
LC/MS (Method A): $t_R$ = 3.4 min, $(M + H)^+$ = 439
IR: 3201.94, 2927.08, 1645.33, 1488.84, 1215.19, 1105.25, 883.43, 735.87 $cm^{-1}$

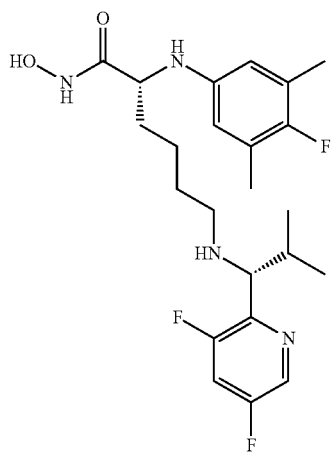 [SMILES: Cc1cc(N[C@H](CCCCN[C@@H](c2ncc(F)cc2F)C(C)C)C(=O)NO)cc(C)c1F]

Name: (R)-6-(((R)-1-(3,5-difluoropyridin-2-yl)-2-methylpropyl)amino)-2-((4-fluoro-3,5-dimethylphenyl)amino)-N-hydroxyhexanamide
Compound: 6
LC/MS (Method A): $t_R$ = 3.5 min, $(M + H)^+$ = 453
IR: 3201.94, 2929.97, 1652.09, 1464.02, 1216.16, 1106.21, 877.64, 759.01 $cm^{-1}$

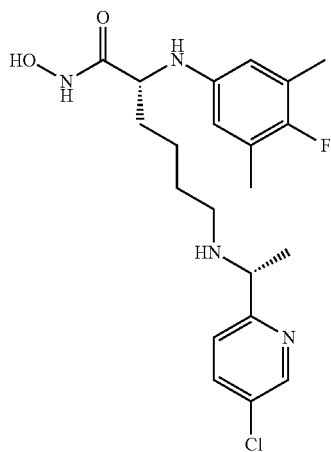 [SMILES: Cc1cc(N[C@H](CCCCN[C@H](C)c2ccc(Cl)cn2)C(=O)NO)cc(C)c1F]

Name: (R)-6-(((R)-1-(5-chloropyridin-2-yl)ethyl)amino)-2-((4-fluoro-3,5-dimethylphenyl)amino)-N-hydroxyhexanamide
Compound: 7
LC/MS (Method A): $t_R$ = 3.3 min, (M + H)$^+$ = 423
IR: 3363.97, 3225.09, 1651.12, 1485.24, 1213.27, 1120.68, 837.13, 752.26 cm$^{-1}$

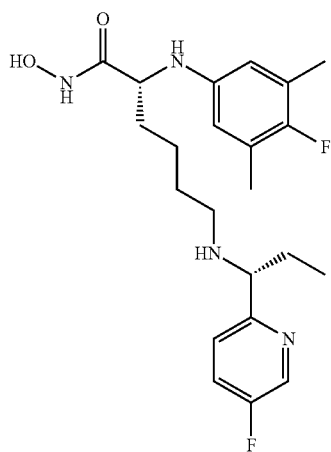 [SMILES: CC[C@@H](NCCCC[C@@H](Nc1cc(C)c(F)c(C)c1)C(=O)NO)c1ccc(F)cn1]

Name: (R)-2-((4-fluoro-3,5-dimethylphenyl)amino)-6-(((R)-1-(5-fluoropyridin-2-yl)propyl)amino)-N-hydroxyhexanamide
Compound: 8
LC/MS (Method A): $t_R$ = 3.3 min, (M + H)$^+$ = 421
IR: 3234.73, 2931.90, 1660.7, 1485.24, 1217.12, 1022.31, 840.99, 758.05 cm$^{-1}$

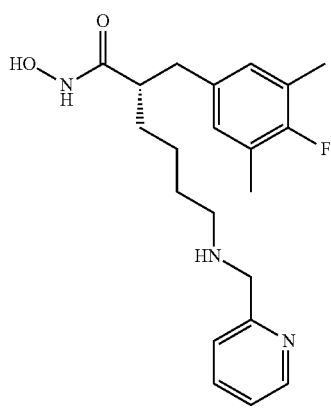 [SMILES: Cc1cc(C[C@H](CCCCNCc2ccccn2)C(=O)NO)cc(C)c1F]

Name: (S)-2-(4-fluoro-3,5-dimethylbenzyl)-N-hydroxy-6-((pyridin-2-ylmethyl)amino)hexanamide
Compound: 9
LC/MS (Method A): $t_R$ = 3.8 min, (M + H)$^+$ = 374
IR: 3404 (br), 3221 (br), 2926, 2861, 1645, 1595, 1487, 1441, 1207, 1144 cm$^{-1}$

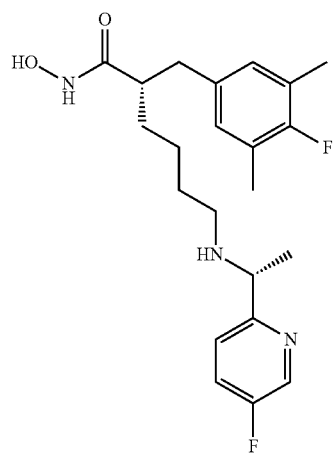 [SMILES: Cc1cc(C[C@H](CCCCN[C@H](C)c2ccc(F)cn2)C(=O)NO)cc(C)c1F]

Name: (S)-2-(4-fluoro-3,5-dimethylbenzyl)-6-(((R)-1-(5-fluoropyridin-2-yl)ethyl)amino)-N-hydroxyhexanamide
Compound: 10
LC/MS (Method A): $t_R$ = 4.1 min, (M + H)$^+$ = 406
IR: 3183.62, 2924.18, 1652.09, 1486.20, 1208.44, 1017.48, 837.13, 760.94 cm$^{-1}$

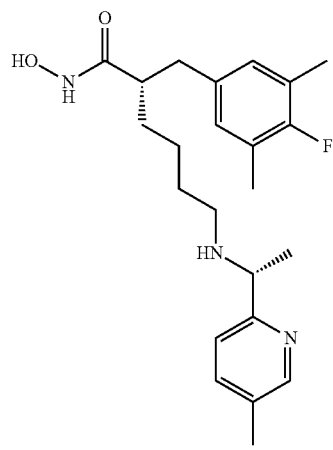 [SMILES: Cc1ccc([C@@H](C)NCCCC[C@@H](Cc2cc(C)c(F)c(C)c2)C(=O)NO)nc1]

Name: (S)-2-(4-fluoro-3,5-dimethylbenzyl)-N-hydroxy-6-(((R)-1-(5-methylpyridin-2-yl)ethyl)amino)hexanamide
Compound: 11
LC/MS (Method A): $t_R$ = 4.2 min, (M + H)$^+$ = 402
IR: 3200.98, 2926.11, 1645.33, 1489.10, 1208.44, 1035.81, 837.13, 756.12 cm$^{-1}$

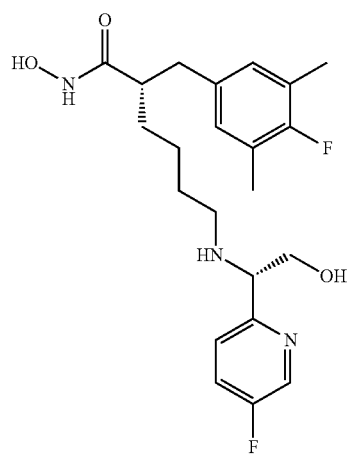 [SMILES: Cc1cc(C[C@H](CCCCN[C@H](CO)c2ccc(F)cn2)C(=O)NO)cc(C)c1F]

Name: (S)-2-(4-fluoro-3,5-dimethylbenzyl)-6-(((S)-1-(5-fluoropyridin-2-yl)-2-hydroxyethyl)amino)-N-hydroxyhexanamide
Compound: 12
LC/MS (Method A): $t_R$ = 3.9 min, (M + H)$^+$ = 422
IR: 3218.34, 2926.11, 1652.09, 1486.20, 1229.66, 1052.20, 760.94 cm$^{-1}$

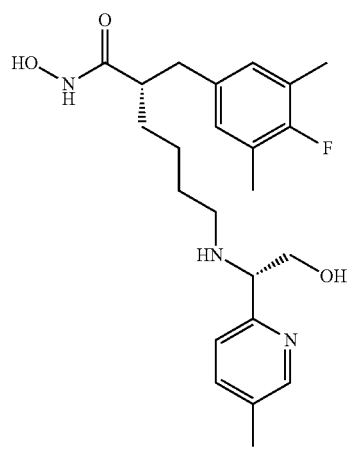 [SMILES: Cc1ccc([C@@H](CO)NCCCC[C@@H](Cc2cc(C)c(F)c(C)c2)C(=O)NO)nc1]

Name: (S)-2-(4-fluoro-3,5-dimethylbenzyl)-N-hydroxy-6-(((S)-2-hydroxy-1-(5-methylpyridin-2-yl)ethyl)amino)hexanamide
Compound: 13
LC/MS (Method A): $t_R$ = 4.0 min, (M + H)$^+$ = 418
IR: 3208.69, 2925.15, 2856.67, 1651.12, 1489.10, 1208.44, 1038.70, 836.17 cm$^{-1}$

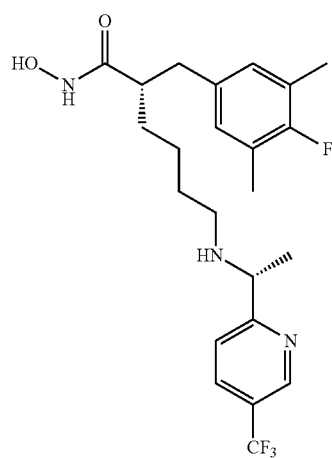 [SMILES: Cc1cc(C[C@H](CCCCN[C@H](C)c2ccc(C(F)(F)F)cn2)C(=O)NO)cc(C)c1F]

Name: (S)-2-(4-fluoro-3,5-dimethylbenzyl)-N-hydroxy-6-(((R)-1-(5-(trifluoromethyl)pyridin-2-yl)ethyl)amino)hexanamide
Compound: 14
LC/MS (Method A): $t_R$ = 3.7 min, (M + H)$^+$ = 456
IR: 3055.35, 1674.27, 1456.30, 1203.62, 1136.11, 840.99, 723.33 cm$^{-1}$

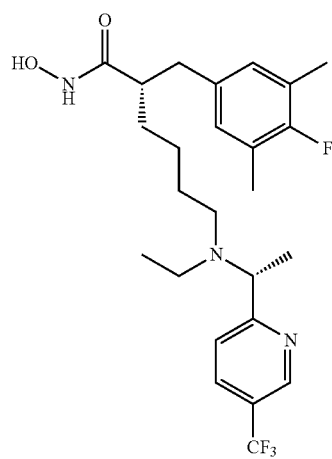 [SMILES: CCN(CCCC[C@@H](Cc1cc(C)c(F)c(C)c1)C(=O)NO)[C@H](C)c1ccc(C(F)(F)F)cn1]

Name: (S)-6-(ethyl((R)-1-(5-(trifluoromethyl)pyridin-2-yl)ethyl)amino)-2-(4-fluoro-3,5-dimethylbenzyl)-N-hydroxyhexanamide
Compound: 15
LC/MS (Method A): $t_R$ = 3.7 min, (M + H)$^+$ = 484
IR: 3207.73, 2931.90, 1645.33, 1489.10, 1327.07, 1134.18, 759.98 cm$^{-1}$

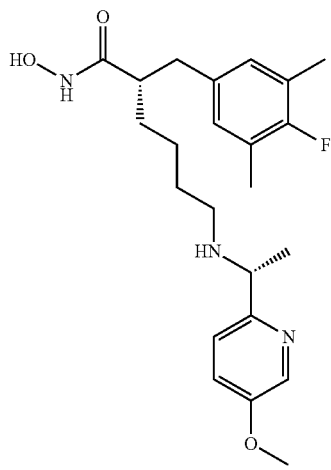 [SMILES: COc1ccc([C@@H](C)NCCCC[C@@H](Cc2cc(C)c(F)c(C)c2)C(=O)NO)nc1]

Name: (S)-2-(4-fluoro-3,5-dimethylbenzyl)-N-hydroxy-6-(((R)-1-(5-methoxypyridin-2-yl)ethyl)amino)hexanamide
Compound: 16
LC/MS (Method A): $t_R$ = 3.4 min, (M + H)$^+$ = 418
IR: 3211.59, 2926.11, 1651.12, 1489.10, 1269.20, 1207.48, 1031.95, 759.98 cm$^{-1}$

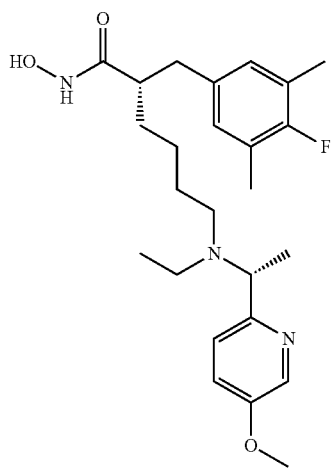 [SMILES: CCN(CCCC[C@@H](Cc1cc(C)c(F)c(C)c1)C(=O)NO)[C@H](C)c1ccc(OC)cn1]

Name: (S)-6-(ethyl((R)-1-(5-methoxypyridin-2-yl)ethyl)amino)-2-(4-fluoro-3,5-dimethylbenzyl)-N-hydroxyhexanamide
Compound: 17
LC/MS (Method A): $t_R$ = 3.5 min, (M + H)$^+$ = 446
IR: 3196.15, 2931.90, 1645.33, 1485.24, 1271.13, 1207.48, 1143.83, 1035.81 cm$^{-1}$

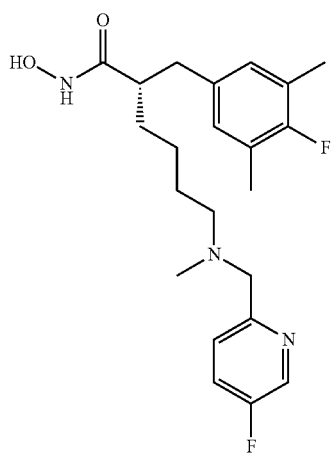 [SMILES: Cc1cc(C[C@H](CCCCN(C)Cc2ccc(F)cn2)C(=O)NO)cc(C)c1F]

Name: (S)-2-(4-fluoro-3,5-dimethylbenzyl)-6-(((5-fluoropyridin-2-yl)methyl)(methyl)amino)-N-hydroxyhexanamide
Compound: 18
LC/MS (Method B): $t_R$ = 4.4 min, (M + H)$^+$ = 406
IR: 3201.94, 2931.90, 1651.12, 1489.10, 1226.77, 1145.75, 1030.02, 864.14 cm$^{-1}$

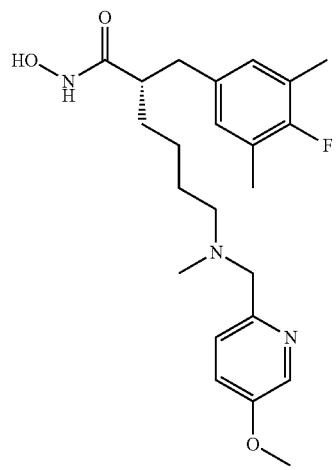 [SMILES: COc1ccc(CN(C)CCCC[C@@H](Cc2cc(C)c(F)c(C)c2)C(=O)NO)nc1]

Name: (S)-2-(4-fluoro-3,5-dimethylbenzyl)-N-hydroxy-6-(((5-methoxypyridin-2-yl)methyl)(methyl)amino)hexanamide
Compound: 19
LC/MS (Method B): $t_R$ = 4.4 min, $(M + H)^+$ = 418
IR: 3194.23, 2939.61, 1651.12, 1489.10, 1273.06, 1207.48, 1033.88, 864.14 cm$^{-1}$

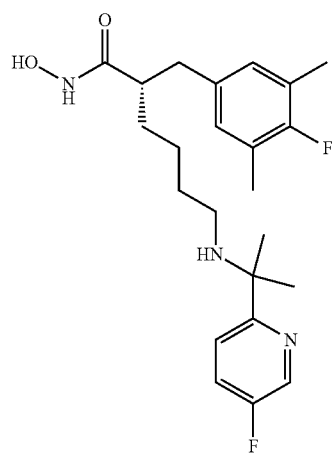 [SMILES: Cc1cc(C[C@H](CCCCNC(C)(C)c2ccc(F)cn2)C(=O)NO)cc(C)c1F]

Name: (S)-2-(4-fluoro-3,5-dimethylbenzyl)-6-((2-(5-fluoropyridin-2-yl)propan-2-yl)amino)-N-hydroxyhexanamide
Compound: 20
LC/MS (Method B): $t_R$ = 4.2 min, $(M + H)^+$ = 420
IR: 3209.86, 2928.04, 1651.12, 1489.10, 1207.48, 1018.45, 837.13, 759.98 cm$^{-1}$

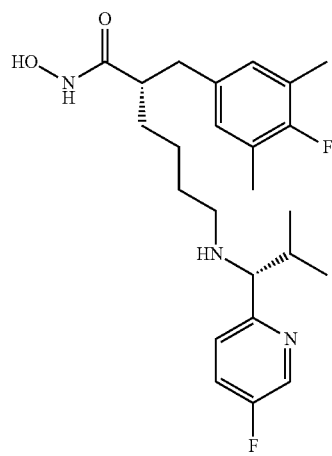 [SMILES: Cc1cc(C[C@H](CCCCN[C@@H](c2ccc(F)cn2)C(C)C)C(=O)NO)cc(C)c1F]

Name: (S)-2-(4-fluoro-3,5-dimethylbenzyl)-6-(((R)-1-(5-fluoropyridin-2-yl)-2-methylpropyl)amino)-N-hydroxyhexanamide
Compound: 21
LC/MS (Method A): $t_R$ = 3.8 min, $(M + H)^+$ = 434
IR: 3162.65, 2926.11, 1645.33, 1485.24, 1209.41, 1018.45, 758.05 cm$^{-1}$

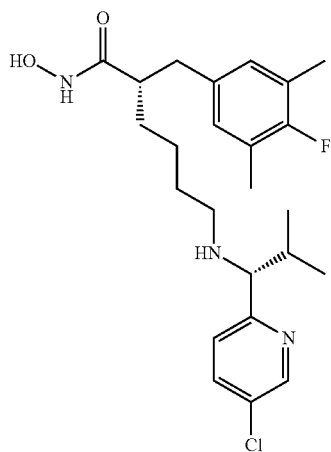 [SMILES: Cc1cc(C[C@H](CCCCN[C@@H](c2ccc(Cl)cn2)C(C)C)C(=O)NO)cc(C)c1F]

Name: (S)-6-(((R)-1-(5-chloropyridin-2-yl)-2-methylpropyl)amino)-2-(4-fluoro-3,5-dimethylbenzyl)-N-hydroxyhexanamide
Compound: 22
LC/MS (Method A): $t_R$ = 3.9 min, $(M + H)^+$ = 450
IR: 3184.58, 2924.18, 1645.33, 1471.74, 1209.41, 1012.66, 756.12 cm$^{-1}$

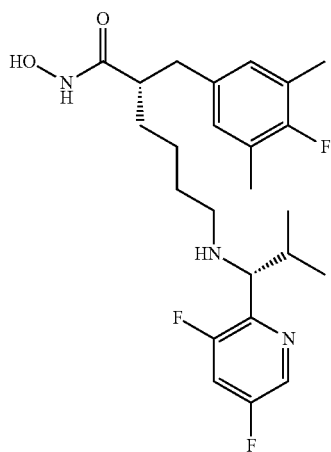 [SMILES: Cc1cc(C[C@H](CCCCN[C@@H](c2ncc(F)cc2F)C(C)C)C(=O)NO)cc(C)c1F]

Name: (S)-6-(((R)-1-(3,5-difluoropyridin-2-yl)-2-methylpropyl)amino)-2-(4-fluoro-3,5-dimethylbenzyl)-N-hydroxyhexanamide
Compound: 23
LC/MS (Method A): $t_R$ = 3.7 min, $(M + H)^+$ = 452
IR: 3189.40, 2927.08, 1652.09, 1470.77, 1209.41, 1104.28, 987.59, 878.60, 760.94 cm$^{-1}$

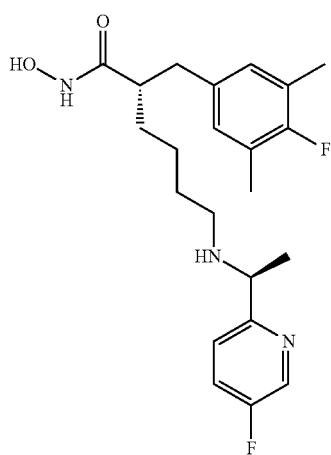 [SMILES: Cc1cc(C[C@H](CCCCN[C@@H](C)c2ccc(F)cn2)C(=O)NO)cc(C)c1F]

Name: (S)-2-(4-fluoro-3,5-dimethylbenzyl)-6-(((S)-1-(5-fluoropyridin-2-yl)ethyl)amino)-N-hydroxyhexanamide
Compound: 24
LC/MS (Method A): $t_R$ = 3.4 min, $(M + H)^+$ = 406
IR: 2918.40, 1622.19, 1480.42, 1220.98, 1105.25, 1008.80, 845.81, 755.16 cm$^{-1}$

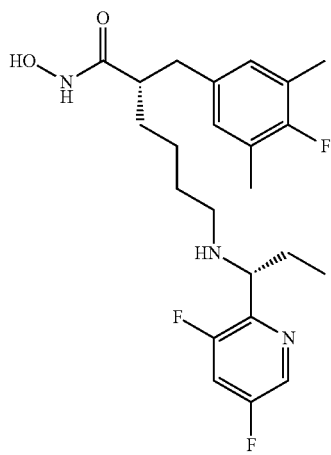 [SMILES: CC[C@@H](NCCCC[C@@H](Cc1cc(C)c(F)c(C)c1)C(=O)NO)c1ncc(F)cc1F]

Name: (S)-6-(((R)-1-(3,5-difluoropyridin-2-yl)propyl)amino)-2-(4-fluoro-3,5-dimethylbenzyl)-N-hydroxyhexanamide
Compound: 25
LC/MS (Method A): $t_R$ = 3.5 min, (M + H)$^+$ = 438
IR: 3196.15, 2926.11, 1652.09, 1475.59, 1209.41, 1104.28, 884.39, 753.23 cm$^{-1}$

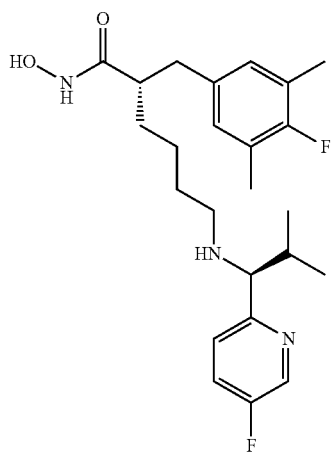 [SMILES: Cc1cc(C[C@H](CCCCN[C@H](c2ccc(F)cn2)C(C)C)C(=O)NO)cc(C)c1F]

Name: (S)-2-(4-fluoro-3,5-dimethylbenzyl)-6-(((S)-1-(5-fluoropyridin-2-yl)-2-methylpropyl)amino)-N-hydroxyhexanamide
Compound: 26
LC/MS (Method A): $t_R$ = 3.6 min, (M + H)$^+$ = 434
IR: 3201.94, 2926.11, 1656.91, 1486.20, 1209.41, 1020.38, 759.01 cm$^{-1}$

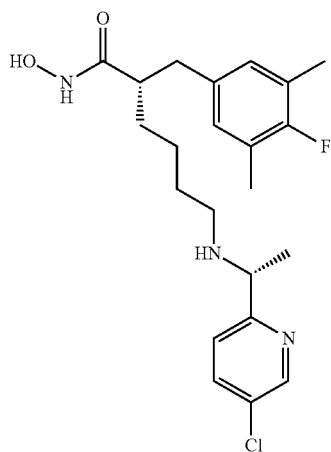 [SMILES: Cc1cc(C[C@H](CCCCN[C@H](C)c2ccc(Cl)cn2)C(=O)NO)cc(C)c1F]

Name: (S)-6-(((R)-1-(5-chloropyridin-2-yl)ethyl)amino)-2-(4-fluoro-3,5-dimethylbenzyl)-N-hydroxyhexanamide
Compound: 27
LC/MS (Method A): $t_R$ = 3.4 min, (M + H)$^+$ = 422
IR: 3176.87, 2924.18, 1652.09, 1486.20, 1207.48, 1110.07, 1011.70, 837.13, 753.23 cm$^{-1}$

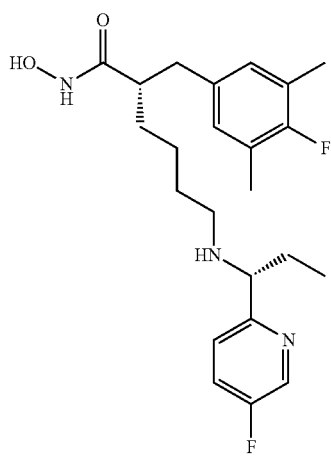 [SMILES: CC[C@@H](NCCCC[C@@H](Cc1cc(C)c(F)c(C)c1)C(=O)NO)c1ccc(F)cn1]

Name: (S)-2-(4-fluoro-3,5-dimethylbenzyl)-6-(((R)-1-(5-fluoropyridin-2-yl)propyl)amino)-N-hydroxyhexanamide
Compound: 28
LC/MS (Method A): $t_R$ = 3.4 min, (M + H)$^+$ = 420
IR: 3183.62, 2925.15, 1652.09, 1489.10, 1229.66, 1144.79, 1017.48, 839.06, 722.37 cm$^{-1}$

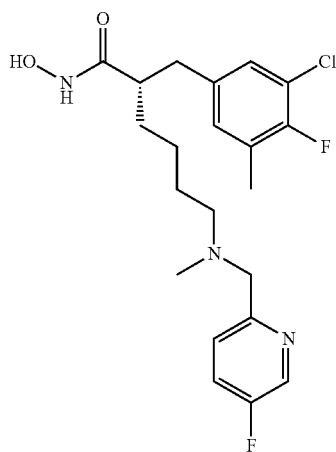 [SMILES: Cc1cc(C[C@H](CCCCN(C)Cc2ccc(F)cn2)C(=O)NO)cc(Cl)c1F]

Name: (S)-2-(3-chloro-4-fluoro-5-methylbenzyl)-6-(((5-fluoropyridin-2-yl)methyl)(methyl)amino)-N-hydroxyhexanamide
Compound: 29
LC/MS (Method A): $t_R$ = 3.2 min, (M + H)$^+$ = 426
IR: 3194.23, 2937.68, 1645.33, 1487.17, 1228.70, 1030.02, 866.07, 756.12 cm$^{-1}$

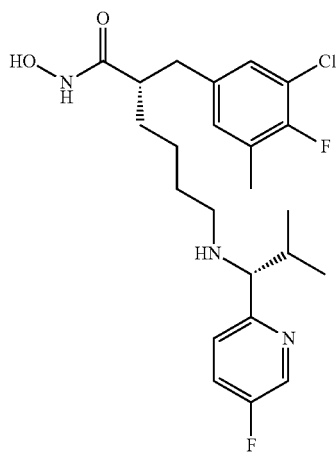 [SMILES: Cc1cc(C[C@H](CCCCN[C@@H](c2ccc(F)cn2)C(C)C)C(=O)NO)cc(Cl)c1F]

Name: (S)-2-(3-chloro-4-fluoro-5-methylbenzyl)-6-(((R)-1-(5-fluoropyridin-2-yl)-2-methylpropyl)amino)-N-hydroxyhexanamide
Compound: 30
LC/MS (Method A): $t_R$ = 3.9 min, (M + H)$^+$ = 454
IR: 3182.65, 2927.97, 1645.33, 1485.24, 1217.12, 1018.45, 868.00, 758.05 cm$^{-1}$

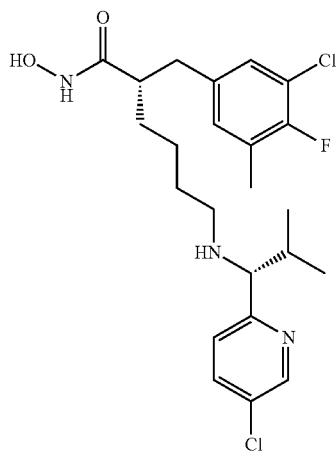 [SMILES: Cc1cc(C[C@H](CCCCN[C@@H](c2ccc(Cl)cn2)C(C)C)C(=O)NO)cc(Cl)c1F]

Name: (S)-2-(3-chloro-4-fluoro-5-methylbenzyl)-6-(((R)-1-(5-chloropyridin-2-yl)-2-methylpropyl)amino)-N-hydroxyhexanamide
Compound: 31
LC/MS (Method A): $t_R$ = 3.9 min, (M + H)$^+$ = 470
IR: 3188.44, 2931.90, 1647.26, 1489.10, 1107.18, 1012.66, 756.12 cm$^{-1}$

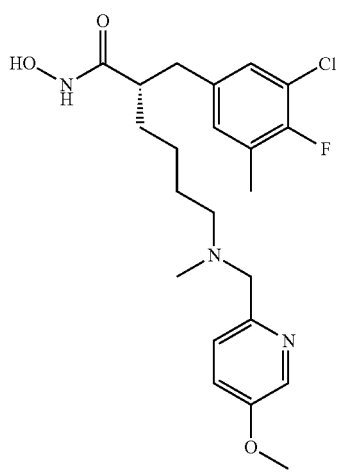 [SMILES: COc1ccc(CN(C)CCCC[C@@H](Cc2cc(C)c(F)c(Cl)c2)C(=O)NO)nc1]

Name: (S)-2-(3-chloro-4-fluoro-5-methylbenzyl)-N-hydroxy-6-(((5-methoxypyridin-2-yl)methyl)(methyl)amino)hexanamide
Compound: 32
LC/MS (Method B): $t_R$ = 4.3 min, (M + H)$^+$ = 438
IR: 3200.01, 2937.68, 1651.12, 1485.24, 1274.99, 1031.95, 866.07, 756.12 cm$^{-1}$

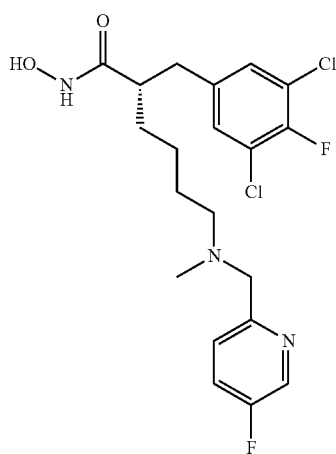 [SMILES: CN(CCCC[C@@H](Cc1cc(Cl)c(F)c(Cl)c1)C(=O)NO)Cc1ccc(F)cn1]

Name: (S)-2-(3,5-dichloro-4-fluorobenzyl)-6-(((5-fluoropyridin-2-yl)methyl)(methyl)amino)-N-hydroxyhexanamide
Compound: 33
LC/MS (Method A): $t_R$ = 3.3 min, (M + H)$^+$ = 446
IR: 3201.94, 2937.68, 1651.12, 1485.24, 1269.20, 1028.09, 756.12 cm$^{-1}$

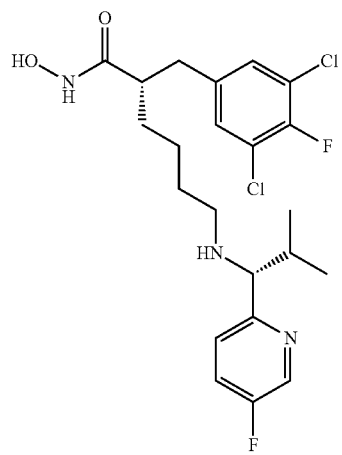 [SMILES: CC(C)[C@@H](NCCCC[C@@H](Cc1cc(Cl)c(F)c(Cl)c1)C(=O)NO)c1ccc(F)cn1]

Name: (S)-2-(3,5-dichloro-4-fluorobenzyl)-6-(((R)-1-(5-fluoropyridin-2-yl)-2-methylpropyl)amino)-N-hydroxyhexanamide
Compound: 34
LC/MS (Method A): $t_R$ = 4.0 min, (M + H)$^+$ = 474
IR: 3194.23, 2931.90, 1645.33, 1487.17, 1269.20, 869.92, 709.83 cm$^{-1}$

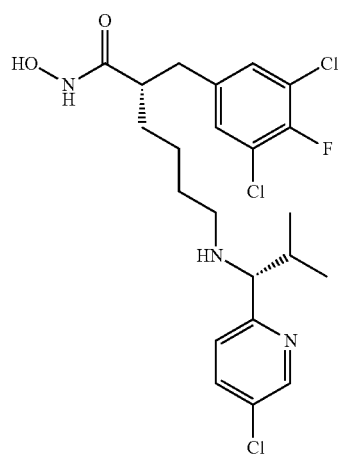 [SMILES: CC(C)[C@@H](NCCCC[C@@H](Cc1cc(Cl)c(F)c(Cl)c1)C(=O)NO)c1ccc(Cl)cn1]

Name: (S)-6-(((R)-1-(5-chloropyridin-2-yl)-2-methylpropyl)amino)-2-(3,5-dichloro-4-fluorobenzyl)-N-hydroxyhexanamide
Compound 35
LC/MS (Method A): $t_R$ = 4.0 min, (M + H)$^+$ = 490
IR: 3196.15, 2933.83, 1645.33, 1487.17, 1269.20, 1112.96, 869.92, 707.90 cm$^{-1}$

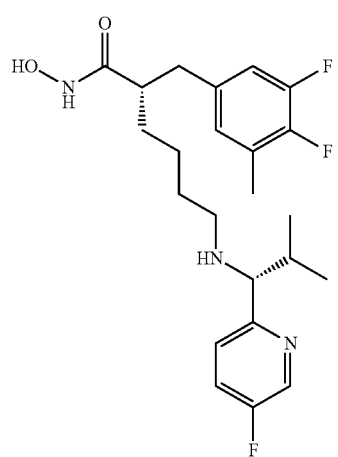

Name: (S)-2-(3,4-difluoro-5-methylbenzyl)-6-(((R)-1-(5-fluoropyridin-2-yl)-2-methylpropyl)amino)-N-hydroxyhexanamide
Compound: 36
LC/MS (Method A): $t_R$ = 3.6 min, (M + H)$^+$ = 438
IR: 3213.51, 2929.97, 1651.12, 1504.53, 1230.63, 1045.45, 862.21, 759.98 cm$^{-1}$

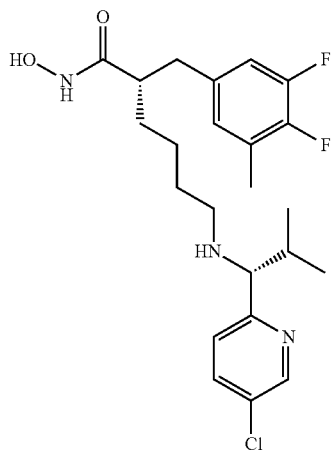 [SMILES: Cc1cc(C[C@H](CCCCN[C@@H](c2ccc(Cl)cn2)C(C)C)C(=O)NO)cc(F)c1F]

Name: (S)-6-(((R)-1-(5-chloropyridin-2-yl)-2-methylpropyl)amino)-2-(3,4-difluoro-5-methylbenzyl)-N-hydroxyhexanamide
Compound: 37
LC/MS (Method A): $t_R$ = 3.8 min, (M + H)$^+$ = 454
IR: 3182.65, 2928.04, 1645.33, 1506.46, 1215.19, 1107.18, 1012.66, 862.21 cm$^{-1}$

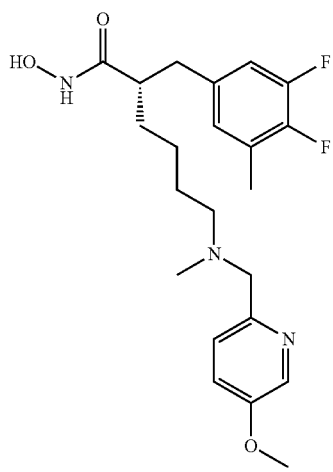 [SMILES: COc1ccc(CN(C)CCCC[C@@H](Cc2cc(C)c(F)c(F)c2)C(=O)NO)nc1]

Name: (S)-2-(3,4-difluoro-5-methylbenzyl)-N-hydroxy-6-(((5-methoxypyridin-2-yl)methyl)(methyl)amino)hexanamide
Compound: 38
LC/MS (Method A): $t_R$ = 3.2 min, (M + H)$^+$ = 422
IR: 3188.44, 2937.68, 1649.19, 1504.53, 1273.06, 1215.19, 1031.95, 754.19 cm$^{-1}$

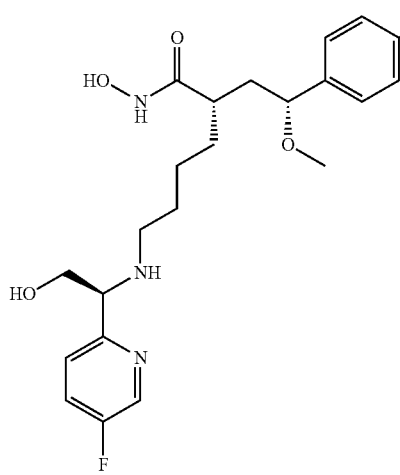

Name: (S)-2-((R)-2-(4-fluorophenyl)-2-methoxyethyl)-6-(((S)-1-(5-fluoropyridin-2-yl)-2-hydroxyethyl)amino)-N-hydroxyhexanamide
Compound: 39
LC/MS (Method A): 438 (M + H$^+$) $t_R$ = 3.6
IR: 3190, 2935, 1863, 1821, 1652, 1558, 1539, 1506, 1229, 1120, 1070, 839 cm$^{-1}$

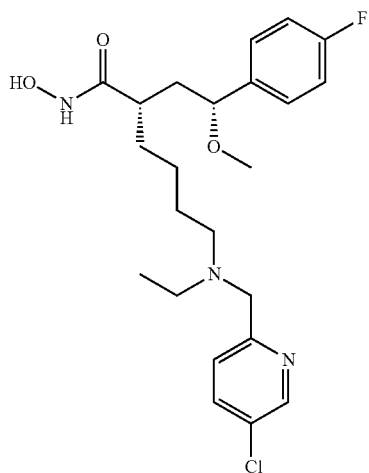 [SMILES: CCN(CCCC[C@@H](C[C@@H](OC)c1ccc(F)cc1)C(=O)NO)Cc1ccc(Cl)cn1]

Name: (S)-6-(((5-chloropyridin-2-yl)methyl)(ethyl)amino)-2-((R)-2-(4-fluorophenyl)-2-methoxyethyl)-N-hydroxyhexanamide
Compound: 40
LC/MS (Method A): 452 (M + H$^+$) t$_R$ = 3.3
IR: 3371, 3174, 2926, 1712, 1651, 1506, 1469, 1220, 1111, 1016 cm$^{-1}$

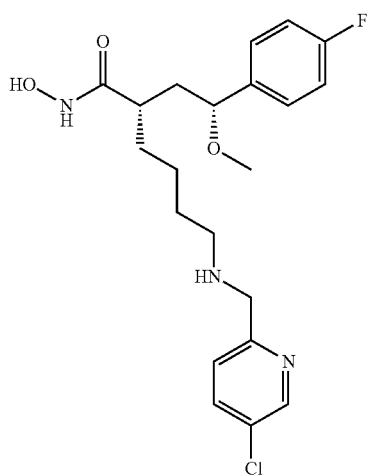 [SMILES: CO[C@H](C[C@H](CCCCNCc1ccc(Cl)cn1)C(=O)NO)c1ccc(F)cc1]

Name: (S)-6-(((5-chloropyridin-2-yl)methyl)amino)-2-((R)-2-(4-fluorophenyl)-2-methoxyethyl)-N-hydroxyhexanamide
Compound: 41
LC/MS (Method A): 424 (M + H$^+$) t$_R$ = 3.0
IR: 3356, 3194, 2920, 1651, 1454, 1222, 1107, 1018 cm$^{-1}$

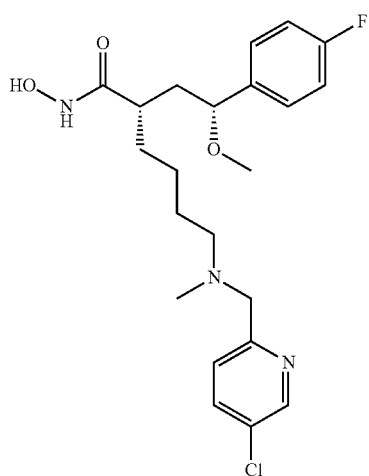 [SMILES: CO[C@H](C[C@H](CCCCN(C)Cc1ccc(Cl)cn1)C(=O)NO)c1ccc(F)cc1]

Name: (S)-6-(((5-chloropyridin-2-yl)methyl)(methyl)amino)-2-((R)-2-(4-fluorophenyl)-2-methoxyethyl)-N-hydroxyhexanamide
Compound: 42
LC/MS (Method A): 438 (M + H$^+$) t$_R$ = 3.1
IR: 381, 3182, 2926, 1712, 1651, 1604, 1506, 1469, 1220, 1111, 1016 cm$^{-1}$

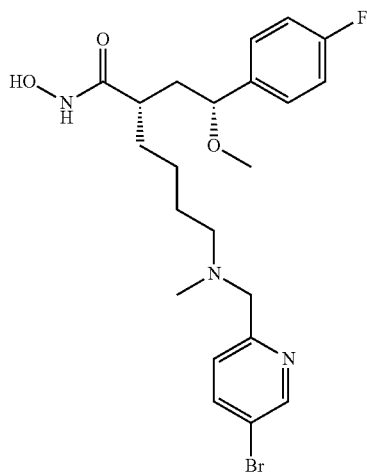 [SMILES: CO[C@H](C[C@H](CCCCN(C)Cc1ccc(Br)cn1)C(=O)NO)c1ccc(F)cc1]

Name: (S)-6-(((5-bromopyridin-2-yl)methyl)(methyl)amino)-2-((R)-2-(4-fluorophenyl)-2-methoxyethyl)-N-hydroxyhexanamide
Compound: 43
LC/MS (Method A): 482 (M + H⁺) $t_R$ = 3.1
IR: 3431, 3173, 2926, 2717, 1712, 1652, 1506, 1469, 1220, 1109, 1095, 1010 cm⁻¹

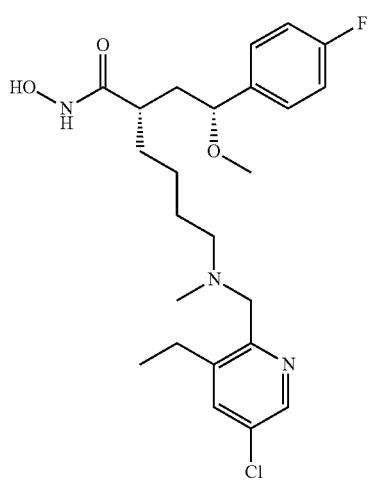 [SMILES: CCc1cc(Cl)cnc1CN(C)CCCC[C@@H](C[C@@H](OC)c1ccc(F)cc1)C(=O)NO]

Name: (S)-6-(((5-chloro-3-ethylpyridin-2-yl)methyl)(methyl)amino)-2-((R)-2-(4-fluorophenyl)-2-methoxyethyl)-N-hydroxyhexanamide
Compound: 44
LC/MS (Method A): 466 (M + H⁺) $t_R$ = 3.5
IR: 3394, 3173, 2931, 2868, 1651, 1604, 1504, 1462, 1442, 1220, 1157, 1112, 1072, 889 cm⁻¹

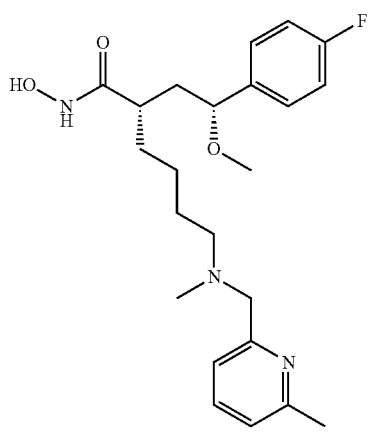 [SMILES: CO[C@H](C[C@H](CCCCN(C)Cc1cccc(C)n1)C(=O)NO)c1ccc(F)cc1]

Name: (S)-2-((R)-2-(4-fluorophenyl)-2-methoxyethyl)-N-hydroxy-6-(methyl((6-methylpyridin-2-yl)methyl)amino)hexanamide
Compound: 45
LC/MS (Method A): 418 (M + H⁺) $t_R$ = 3.1
IR: 3346, 3194, 2926, 2866, 2827, 1651, 1602, 1506, 1462, 1220, 1157, 1111, 1095, 1074, 1004 cm⁻¹

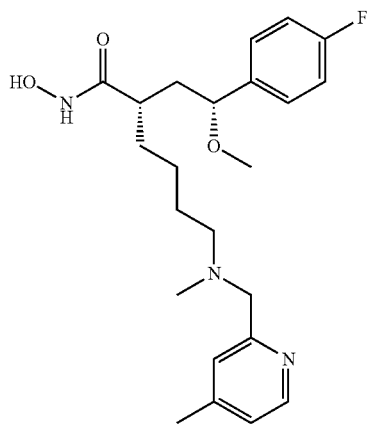 [SMILES: CO[C@H](C[C@H](CCCCN(C)Cc1cc(C)ccn1)C(=O)NO)c1ccc(F)cc1]

Name: (S)-2-((R)-2-(4-fluorophenyl)-2-methoxyethyl)-N-hydroxy-6-(methyl((4-methylpyridin-2-yl)methyl)amino)hexanamide
Compound: 46
LC/MS (Method A): 418 (M + H$^+$) $t_R$ = 3.0
IR: 3317, 3194, 2931, 2868, 2827, 1651, 1608, 1508, 1469, 1454, 1315, 1220, 1111, 1095, 1074, 908 cm$^{-1}$

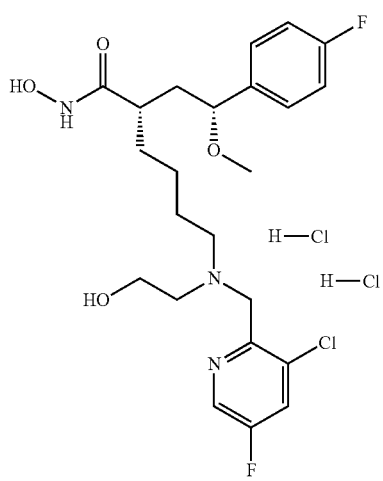

Name: (S)-6-(((3-chloro-5-fluoropyridin-2-yl)methyl)(2-hydroxyethyl)amino)-2-((R)-2-(4-fluorophenyl)-2-methoxyethyl)-N-hydroxyhexanamide
Compound: 47
LC/MS (Method A): 486 (M + H$^+$) $t_R$ = 3.1
IR: 3362, 3165, 3030, 1716, 1653, 1506, 1456, 1259, 1222, 1095, 993, 933 cm$^{-1}$

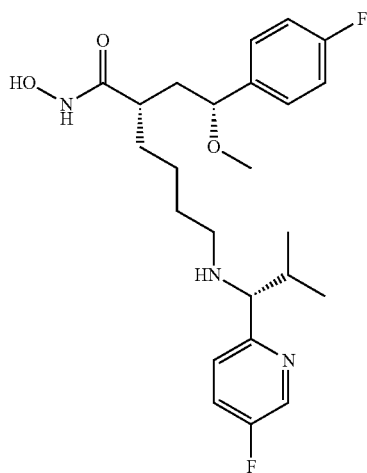 [SMILES: CO[C@H](C[C@H](CCCCN[C@@H](c1ccc(F)cn1)C(C)C)C(=O)NO)c1ccc(F)cc1]

Name: (S)-2-((R)-2-(4-fluorophenyl)-2-methoxyethyl)-6-(((R)-1-(5-fluoropyridin-2-yl)-2-methylpropyl)amino)-N-hydroxyhexanamide
Compound: 48
LC/MS (Method A): 450 (M + H$^+$) $t_R$ = 3.4
IR: 3203, 2926, 2860, 1653, 1558, 1506, 1386, 1222, 1114, 1030, 983, 941 cm$^{-1}$

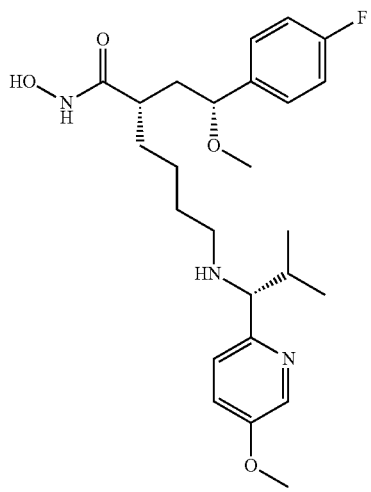 [SMILES: COc1ccc([C@H](NCCCC[C@@H](C[C@@H](OC)c2ccc(F)cc2)C(=O)NO)C(C)C)nc1]

Name: (S)-2-((R)-2-(4-fluorophenyl)-2-methoxyethyl)-N-hydroxy-6-(((R)-1-(5-methoxypyridin-2-yl)-2-methylpropyl)amino)hexanamide
Compound: 49
LC/MS (Method A): 462 (M + H$^+$) $t_R$ = 3.4
IR: 3219, 2926, 2856, 1653, 1558, 1506, 1456, 1269, 1220, 1114, 1031, 941, 891 cm$^{-1}$

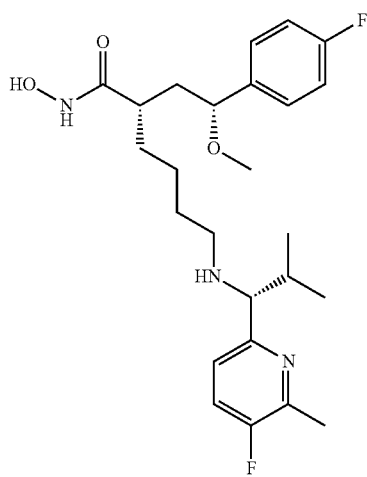 [SMILES: CO[C@H](C[C@H](CCCCN[C@@H](c1ccc(F)c(C)n1)C(C)C)C(=O)NO)c1ccc(F)cc1]

Name: (S)-6-(((R)-1-(5-fluoro-6-methylpyridin-2-yl)-2-methylpropyl)amino)-2-((R)-2-(4-fluorophenyl)-2-methoxyethyl)-N-hydroxyhexanamide
Compound: 50
LC/MS (Method A): 464 (M + H$^+$) $t_R$ = 3.6
IR: 3219, 2926, 2868, 1653, 1558, 1506, 1456, 1222, 1157, 1114, 1037, 987, 941 cm$^{-1}$

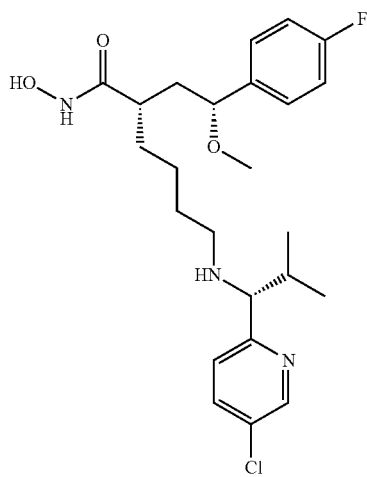 [SMILES: CO[C@H](C[C@H](CCCCN[C@@H](c1ccc(Cl)cn1)C(C)C)C(=O)NO)c1ccc(F)cc1]

Name: (S)-6-(((R)-1-(5-chloropyridin-2-yl)-2-methylpropyl)amino)-2-((R)-2-(4-fluorophenyl)-2-methoxyethyl)-N-hydroxyhexanamide
Compound: 51
LC/MS (Method A): 466 (M + H$^+$) $t_R$ = 3.3
IR: 3196, 2929, 2864, 2825, 1652, 1604, 1558, 1506, 1458, 1373, 1222, 1111, 1014 cm$^{-1}$

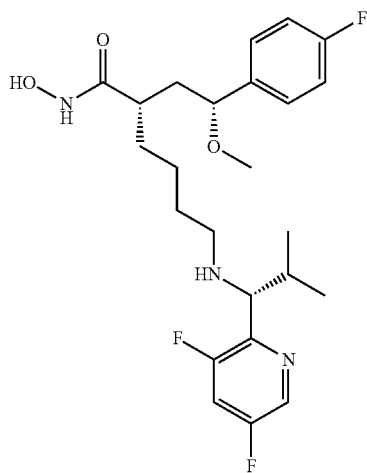 [SMILES: CO[C@H](C[C@H](CCCCN[C@@H](c1ncc(F)cc1F)C(C)C)C(=O)NO)c1ccc(F)cc1]

Name: (S)-6-(((R)-1-(3,5-difluoropyridin-2-yl)-2-methylpropyl)amino)-2-((R)-2-(4-fluorophenyl)-2-methoxyethyl)-N-hydroxyhexanamide
Compound: 52
LC/MS (Method A): 468 (M + H$^+$) $t_R$ = 3.3
IR: 3338, 3208, 2934, 2871, 1652, 1605, 1509, 1464, 1418, 1290, 1221, 1109, 989, 877 cm$^{-1}$

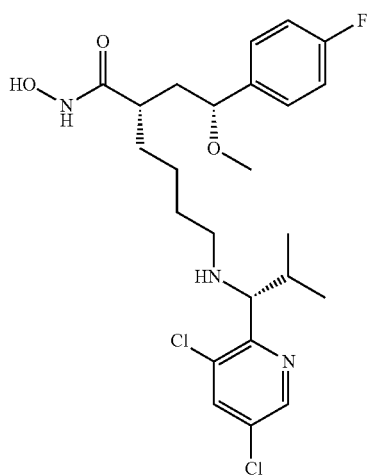 [SMILES: CO[C@H](C[C@H](CCCCN[C@@H](c1ncc(Cl)cc1Cl)C(C)C)C(=O)NO)c1ccc(F)cc1]

Name: (S)-6-(((R)-1-(3,5-dichloropyridin-2-yl)-2-methylpropyl)amino)-2-((R)-2-(4-fluorophenyl)-2-methoxyethyl)-N-hydroxyhexanamide
Compound: 53
LC/MS (Method A): 500 (M + H$^+$) $t_R$ = 3.7
IR: 3218, 2932, 1652, 1605, 1505, 1429, 1372, 1222, 1110, 1048 cm$^{-1}$

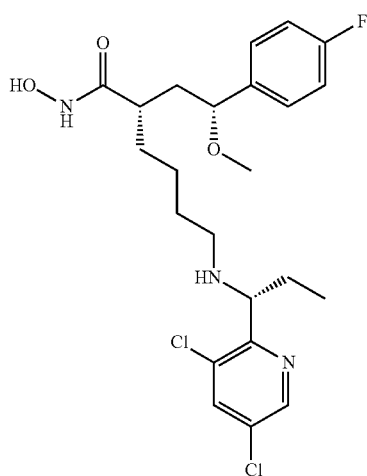 [SMILES: CC[C@@H](NCCCC[C@@H](C[C@@H](OC)c1ccc(F)cc1)C(=O)NO)c1ncc(Cl)cc1Cl]

Name: (S)-6-(((R)-1-(3,5-dichloropyridin-2-yl)propyl)amino)-2-((R)-2-(4-fluorophenyl)-2-methoxyethyl)-N-hydroxyhexanamide
Compound: 54
LC/MS (Method A): 486 (M + H$^+$) $t_R$ = 3.6
IR: 3226, 2932, 2860, 1652, 1505, 1429, 1377, 1221, 1113, 1048, 891 cm$^{-1}$

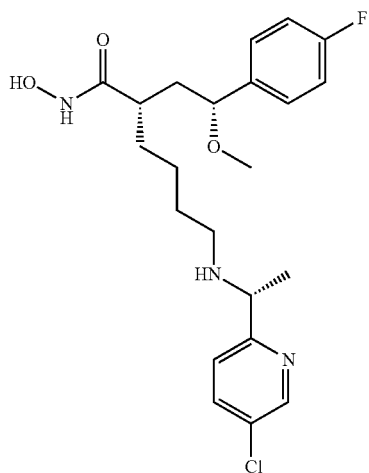 [SMILES: CO[C@H](C[C@H](CCCCN[C@H](C)c1ccc(Cl)cn1)C(=O)NO)c1ccc(F)cc1]

Name: (S)-6-(((R)-1-(5-chloropyridin-2-yl)ethyl)amino)-2-((R)-2-(4-fluorophenyl)-2-methoxyethyl)-N-hydroxyhexanamide
Compound: 55
LC/MS (Method A): 438 (M + H$^+$) t$_R$ = 3.2
IR: 3296, 2931, 1860, 1660, 1506, 1464, 1373, 1222, 1112, 1014, 837, 736 cm$^{-1}$

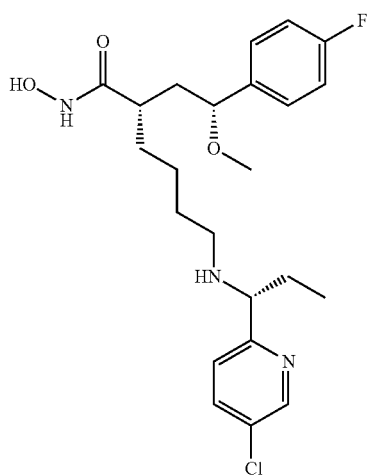 [SMILES: CC[C@@H](NCCCC[C@@H](C[C@@H](OC)c1ccc(F)cc1)C(=O)NO)c1ccc(Cl)cn1]

Name: (S)-6-(((R)-1-(5-chloropyridin-2-yl)propyl)amino)-2-((R)-2-(4-fluorophenyl)-2-methoxyethyl)-N-hydroxyhexanamide
Compound: 56
LC/MS (Method A): 438 (M + H$^+$) t$_R$ = 3.2
IR: 3209, 2926, 1651, 1506, 1464, 1373, 1222, 1111, 1014, 837, 673 cm$^{-1}$

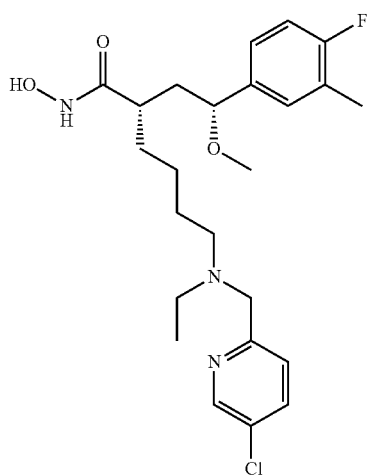 [SMILES: CCN(CCCC[C@@H](C[C@@H](OC)c1ccc(F)c(C)c1)C(=O)NO)Cc1ccc(Cl)cn1]

Name: (S)-6-(((5-chloropyridin-2-yl)methyl)(ethyl)amino)-2-((R)-2-(4-fluoro-3-methylphenyl)-2-methoxyethyl)-N-hydroxyhexanamide
Compound: 57
LC/MS (Method A): 466 (M + H$^+$) t$_R$ = 3.5
IR: 3198, 2931, 2860, 2820, 1653, 1504, 1467, 1371, 1249, 1371, 1249, 1203, 1111, 1014 cm$^{-1}$

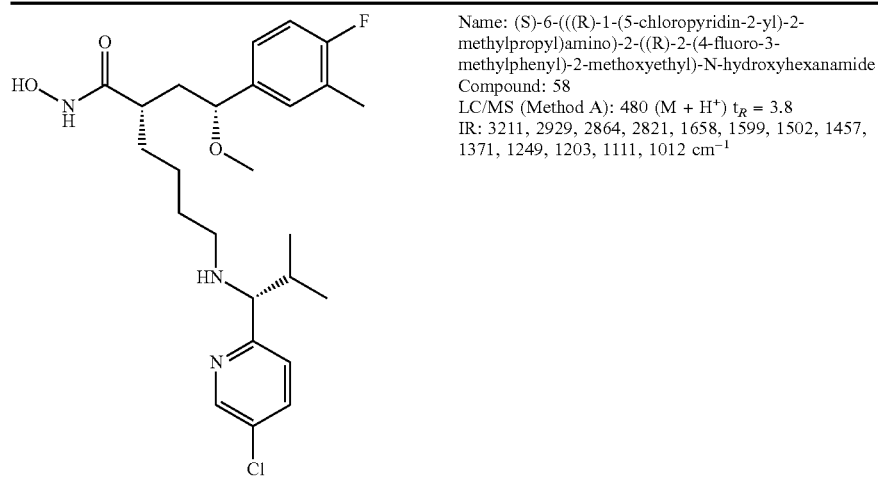

Name: (S)-6-(((R)-1-(5-chloropyridin-2-yl)-2-methylpropyl)amino)-2-((R)-2-(4-fluoro-3-methylphenyl)-2-methoxyethyl)-N-hydroxyhexanamide
Compound: 58
LC/MS (Method A): 480 (M + H$^+$) t$_R$ = 3.8
IR: 3211, 2929, 2864, 2821, 1658, 1599, 1502, 1457, 1371, 1249, 1203, 1111, 1012 cm$^{-1}$

Definitions

The terms "a", "an" and "the" as used herein are defined to mean one or more and include the plural unless the context is inappropriate.

The term "Bacillus anthracis infection" includes any state, diseases, or disorders caused or which result from exposure or alleged exposure to B. anthracis or another member of the Bacillus cereus group of bacteria.

As used herein, the term "edema factor" or "EF" refers to wild-type full-length edema factor of Bacillus anthracis (See SEQ ID NO:3 and Genbank accession number: AAA79215; Robertson, et al, Gene. 1988 Dec. 20; 73(2): 363-71).

As used herein, the term "lethal factor" or "LF" refers to wild-type full-length lethal factor of Bacillus anthracis (See SEQ ID NO:2 and Genbank accession number: AAM26117; Read, et al., Science. 2002 Jun. 14; 296(5575):2028-33)).

As used herein, the term "protective antigen" or "PA" refers to the wild-type full-length protective antigen of B. anthracis (See SEQ ID NO:1 and Genbank accession number: AAA22637; Welkos, et al., J. Gene. 1988 Sep. 30; 69(2):287-300).

The term "effective amount" refers to the amount of compound which, when administered to a human or animal, elicits an immune response, prevents, reduces or lessens B. anthracis infection, causes a reduction in reactivity or inhibits the spread and proliferation of B. anthracis disease. The effective amount is readily determined by one of skill in the art following routine procedures.

The term "compound," as used herein, includes salts, solvates and polymorphs of the compound, as well as the free base. In certain embodiments, the solvate is a hydrate. A solvate is a stable, solid or semi-solid form of a compound that comprises either a non-stoichiometric or a stoichiometric equivalent of solvent. If the solvent is water, the solvate is a hydrate. In certain embodiments, the hydrate has a stoichiometric equivalent of water chosen from about 0, about 0.5, and about 1 H$_2$O molecule; that is, the hydrate is anhydrous, a hemihydrate, or a monohydrate. Non-stoichiometric hydrates and stoichiometric hydrates are both contemplated. As further discussed below, a polymorph is a distinct crystalline form of a compound. A compound may be, for example, a polymorph of a free base, a polymorph of a salt, a polymorph of a hydrate, or a polymorph of a hydrate of a salt of a compound, and so forth.

The term "inhibition" (and by extension, "inhibitor") as used herein encompasses all forms of functional protein (enzyme, kinase, receptor, channel, etc., for example) inhibition, including neutral antagonism, inverse agonism, competitive inhibition, and non-competitive inhibition (such as allosteric inhibition). Inhibition may be phrased in terms of an IC$_{50}$ or K$_i$ value.

As used herein, reference to "treatment" or "treating" of a subject is intended to include prophylaxis.

As used herein, the term "medicament" refers to any substance or combination of substances that has a beneficial and/or therapeutic effect.

As used herein, the term "subject" (as in the subject of the treatment) means both mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like.

The term "subject" does not denote a particular age or sex.

The term "acyl," as used herein, alone or in combination, refers to a carbonyl attached to an alkenyl, alkyl, aryl, cycloalkyl, heteroaryl, heterocycle, or any other moiety where the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon group having one or more double bonds and containing from 2 to 20 carbon atoms. In certain embodiments, the alkenyl will comprise from 2 to 6 carbon atoms. The term "alkenylene" refers to a carbon-carbon double bond system attached at two or more positions such as ethenylene [—CH═CH—]. Examples of suitable alkenyl groups include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl group containing from 1 to 20 carbon atoms. In certain embodiments, the alkyl group will comprise from 1 to 10 carbon atoms. In further embodiments, the alkyl group will comprise from 1 to 6 carbon atoms. In still further embodiments, the alkyl group will comprise from 1 to 4 carbon atoms. Alkyl groups may be optionally substituted as defined herein. Examples of alkyl groups include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The terms "amido" is interchangeable with "carbamoyl," and as used herein, alone or in combination, refer to an amino group as described below attached to the parent molecular moiety through a carbonyl group, or vice versa. The term "C-amido" as used herein, alone or in combination, refers to a —C(O)—NR$_2$ group with R as defined herein. The term "N-amido" as used herein, alone or in combination, refers to a RC(O)NH— group, with R as defined herein. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "halo," or "halogen," as used herein, alone or in combination, refers to fluorine, chlorine, bromine, or iodine.

The term "halo," or "halogen," as used herein, alone or in combination, refers to fluorine, chlorine, bromine, or iodine.

The term "hydroxy," as used herein, alone or in combination, refers to —OH.

The term "hydroxyalkyl," as used herein, alone or in combination, refers to a hydroxy group attached to the parent molecular moiety through an alkyl group.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkanoyl, lower heterocycloalkyl, lower haloalkyl, lower perhaloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, hydrogen, halogen, hydroxy, amino, lower alkylamino, arylamino, amido, nitro, C(O)CH$_3$, CO$_2$CH$_3$, CO$_2$H, and pyridinyl. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The compounds disclosed herein may have a particular spatial arrangement of substituents on the aromatic rings, which is related to the structure activity relationship demonstrated by the compound class. Often such substitution arrangement is denoted by a numbering system; however, numbering systems are often not consistent between different ring systems. In six-membered aromatic systems, the spatial arrangements are specified by the common nomenclature "para" for 1,4-substitution, "meta" for 1,3-substitution and "ortho" for 1,2-substitution as shown below.

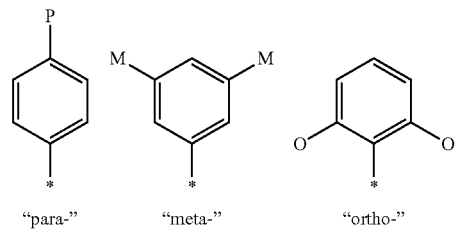

Asymmetric centers exist in the compounds disclosed herein. These centers are designated by the symbols "R" or "S," depending on the configuration of substituents around the chiral carbon atom. It should be understood that embodiments herein encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art.

Examples

The following non-limiting examples, given by way of illustration, is demonstrative of the present embodiments of the present disclosure, that the compounds disclosed herein are useful for treating *B. anthracis* and/or inhibiting LF. Parts and percentages are by weight unless otherwise indicated. As used herein, "room temperature" refers to a temperature of from about 20° C. to about 25° C.

These examples describe the inhibitory effect of the candidate compound on the lethal factor enzyme.

Assay A: LF Fluorescent peptide based proteolytic assay.

Assay Procedure

A fluorescence resonance energy transfer (FRET) assay was used to determine the inhibition kinetics and $K_i$ values with MCA-KKVYPYPME-Dap(Dnp)-$NH_2$ as the peptide substrate (AnaSpec, Fremont, Calif.) Peptide cleavage was measured as an increase in fluorescence with $\lambda_{ex}$=324 nm, $\lambda_{em}$=395 nm. The 100 μL reaction contained 0.5 nM LF 263-C catalytic domain in 20 mM HEPES pH 7.4, 0.1% Tween-20, 0.5 mg/mL BSA and 40 μM peptide substrate. The reaction was initiated with enzyme addition and incubated 4 hours (23° C.) to ensure binding equilibrium and achieve a steady state rate of product formation. Steady state rates were used to determine $K_i$ values by fitting to the classical tight-binding equation.

Results of the Assay Measuring Lethal Factor Inhibitory Activity

Specific examples of compounds within the scope of the present embodiments are shown by their respective structural formulas in Tables 2-4, and their activity in the above-described assay is also indicated. Tables 2, 3, and 4 show exemplary compounds of Formula II, III and IV respectively.

TABLE 2

| Cpd # | $R^1$ | $R^2$ | $R^3$ | p | $K_i$ (nM) |
|---|---|---|---|---|---|
| 1 | H | (S)-$CH_2OH$ | 5-Me | 1 | 0.17 |
| 2 | H | (S)-$CH_2OH$ | 5-F | 1 | 0.14 |
| 3 | H | (R)-iPr | 5-F | 1 | 0.20 |
| 4 | H | (R)-iPr | 5-Cl | 1 | 0.45 |
| 5 | H | (R)-Et | 3,5-di-F | 2 | 0.39 |
| 6 | H | (R)-iPr | 3,5-di-F | 2 | 0.28 |

TABLE 2-continued

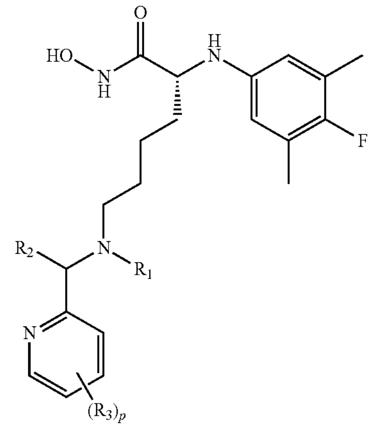

| Cpd # | $R^1$ | $R^2$ | $R^3$ | p | $K_i$ (nM) |
|---|---|---|---|---|---|
| 7 | H | (R)-Me | 5-Cl | 1 | 0.35 |
| 8 | H | (R)-Et | 5-F | 1 | 0.57 |

TABLE 3

| Cpd # | $R^1$ | $R^2$ | $R^3$ | p | R4 (meta) | R4 (para) | R4 (meta') | $K_i$ (nM) |
|---|---|---|---|---|---|---|---|---|
| 9 | H | H | H | 0 | Me | F | Me | 1.0 |
| 10 | H | (R)-Me | 5-F | 1 | Me | F | Me | 0.15 |
| 11 | H | (R)-Me | 5-Me | 1 | Me | F | Me | 0.08 |
| 12 | H | (S)-$CH_2OH$ | 5-F | 1 | Me | F | Me | 0.08 |
| 13 | H | (S)-$CH_2OH$ | 5-Me | 1 | Me | F | Me | 0.07 |
| 14 | H | (R)-Me | 5-$CF_3$ | 1 | Me | F | Me | 1.3 |
| 15 | Et | (R)-Me | 5-$CF_3$ | 1 | Me | F | Me | 3.6 |
| 16 | H | (R)-Me | 5-OMe | 1 | Me | F | Me | 0.31 |
| 17 | Et | (R)-Me | 5-OMe | 1 | Me | F | Me | 4.5 |
| 18 | Me | H | 5-F | 1 | Me | F | Me | 1.6 |
| 19 | Me | H | 5-OMe | 1 | Me | F | Me | 1.4 |
| 20 | H | di-Me | 5-F | 1 | Me | F | Me | 0.19 |
| 21 | H | (R)-iPr | 5-F | 1 | Me | F | Me | 0.11 |
| 22 | H | (R)-iPr | 5-Cl | 1 | Me | F | Me | 0.17 |
| 23 | H | (R)-iPr | 3,5-di-F | 2 | Me | F | Me | 0.25 |
| 24 | H | (S)-Me | 5-F | 1 | Me | F | Me | 0.44 |
| 25 | H | (R)-Et | 3,5-di-F | 2 | Me | F | Me | 0.12 |
| 26 | H | (S)-iPr | 5-F | 1 | Me | F | Me | 0.87 |
| 27 | H | (R)-Me | 5-Cl | 1 | Me | F | Me | 0.08 |
| 28 | H | (R)-Et | 5-F | 1 | Me | F | Me | 0.08 |
| 29 | Me | H | 5-F | 1 | Cl | F | Me | 1.1 |
| 30 | H | (R)-iPr | 5-F | 1 | Cl | F | Me | 0.25 |
| 31 | H | (R)-iPr | 5-Cl | 1 | Cl | F | Me | 0.26 |
| 32 | Me | H | 5-OMe | 1 | Cl | F | Me | 1.5 |
| 33 | Me | H | 5-F | 1 | Cl | F | Cl | 1.6 |
| 34 | H | (R)-iPr | 5-F | 1 | Cl | F | Cl | 0.60 |

TABLE 3-continued

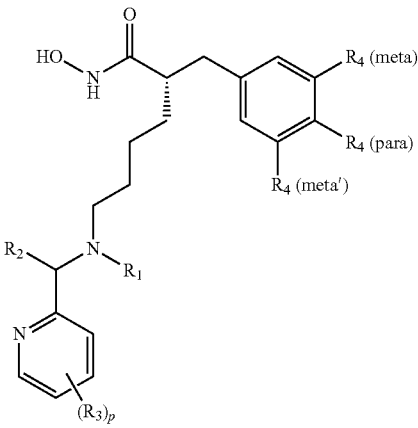

| Cpd # | R¹ | R² | R³ | p | R4 (meta) | R4 (para) | R4 (meta') | $K_i$ (nM) |
|---|---|---|---|---|---|---|---|---|
| 35 | H | (R)-iPr | 5-Cl | 1 | Cl | F | Cl | 0.42 |
| 36 | H | (R)-iPr | 5-F | 1 | F | F | Me | 0.72 |
| 37 | H | (R)-iPr | 5-Cl | 1 | F | F | Me | 0.87 |
| 38 | Me | H | 5-OMe | 1 | F | F | Me | 4.9 |

TABLE 4

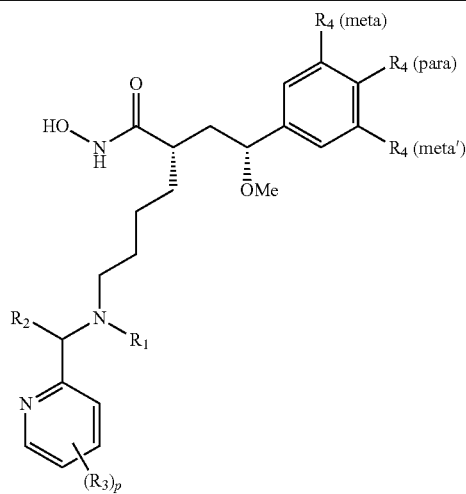

| Cpd # | R¹ | R² | R³ | p | R4 (meta) | R4 (para) | R4 (meta') | $K_i$ (nM) |
|---|---|---|---|---|---|---|---|---|
| 39 | H | (S)-CH₂OH | 5-F | 1 | H | F | H | 1.7 |
| 40 | Et | H | 5-Cl | 1 | H | F | H | 4.5 |
| 41 | H | H | 5-Cl | 1 | H | F | H | 2.2 |
| 42 | Me | H | 5-Cl | 1 | H | F | H | 3.0 |
| 43 | Me | H | 5-Br | 1 | H | F | H | 12.5 |
| 44 | Me | H | 3-Et, 5-Cl | 2 | H | F | H | 6.7 |
| 45 | Me | H | 6-Me | 1 | H | F | H | 15.8 |
| 46 | Me | H | 4-Me | 1 | H | F | H | 14.0 |
| 47 | —CH₂CH₂OH | H | 3-Cl, 5-F | 2 | H | F | H | 53.5 |
| 48 | H | (R)-iPr | 5-F | 1 | H | F | H | 0.62 |
| 49 | H | (R)-iPr | 5-OMe | 1 | H | F | H | 2.7 |
| 50 | H | (R)-iPr | 5-F, 6-Me | 2 | H | F | H | 2.7 |
| 51 | H | (R)-iPr | 5-Cl | 1 | H | F | H | 0.54 |
| 52 | H | (R)-iPr | 3,5-di-F | 2 | H | F | H | 2.1 |
| 53 | H | (R)-iPr | 3,5-di-Cl | 2 | H | F | H | 6.2 |
| 54 | H | (R)-Et | 3,5-di-Cl | 2 | H | F | H | 2.4 |
| 55 | H | (R)-Me | 5-Cl | 1 | H | F | H | 1.6 |
| 56 | H | (R)-Et | 5-Cl | 1 | H | F | H | 0.79 |
| 57 | Et | H | 5-Cl | 1 | H | F | Me | 2.8 |
| 58 | H | (R)-iPr | 5-Cl | 1 | H | F | Me | 2.3 |

All data obtained under Assay A conditions.

What is claimed is:

1. A compound of formula I:

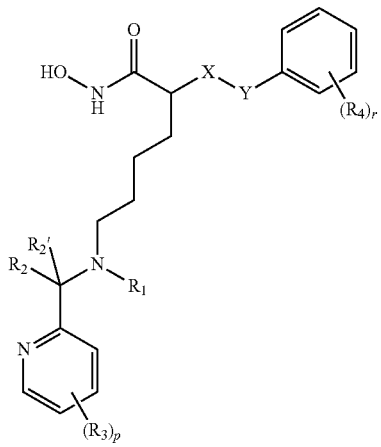

or a pharmaceutically acceptable salt, hydrate or solvate thereof wherein

X is NH or $CH_2$;

Y is a single bond, or $-CHR_5-$;

$R_1$ is H, $C_1$-$C_4$ alkyl, or $C_1$-$C_4$ hydroxyalkyl;

$R_2$ and $R_2'$ are each independently H, $C_1$-$C_4$ alkyl, or $C_1$-$C_4$ hydroxyalkyl;

each $R_3$ is independently H, halo, $-CF_3$, $C_1$-$C_4$ alkyl, or $C_1$-$C_4$ alkoxy, $C_3$ perhaloalkyl;

each $R_4$ is independently H, halo, or $C_1$-$C_4$ alkyl;

$R_5$ is $C_1$-$C_4$ alkoxy;

r is integer from 0 to 3; and p is integer from 0 to 3.

2. The compound of claim 1 wherein X is NH and Y is a single bond.

3. The compound of claim 1 wherein X is $CH_2$ Y is a single bond.

4. The compound of claim 1 wherein X is $CH_2$ and Y is $-CHR_5-$.

5. The compound of claim 4 wherein $R_5$ is methoxy.

6. The compound of claim 1 wherein $R_1$ is H or $C_1$-$C_4$ alkyl.

7. The compound of claim 1 wherein one of $R_2$ and $R_2'$ is H.

8. The compound of claim 5 wherein the other one of $R_2$ and $R_2'$ is $C_1$-$C_4$ alkyl or $C_1$-$C_4$ hydroxyalkyl.

9. The compound of claim 1 wherein p is 1.

10. The compound of claim 1 wherein $R_3$ is $C_1$-$C_4$ alkyl.

11. The compound of claim 1 wherein $R_3$ is methoxy.

12. The compound of claim 1 wherein $R_3$ is halo.

13. The compound of claim 1 wherein $R_3$ is $CF_3$.

14. The compound of claim 1 wherein p is 2.

15. The compound of claim 10 wherein both $R_3$ are halo.

16. The compound of claim 10 wherein one of $R_3$ is halo and the other one of $R_3$ is $C_1$-$C_4$ alkyl.

17. The compound of claim 1 wherein at least one of $R_4$ is halo or methyl.

18. A compound selected from:

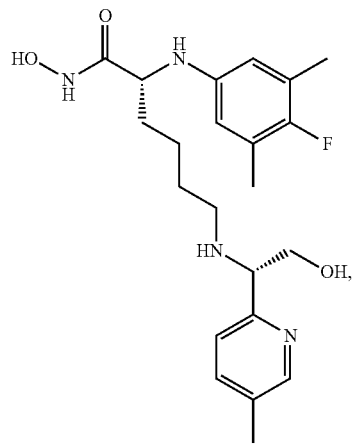

Compound 1

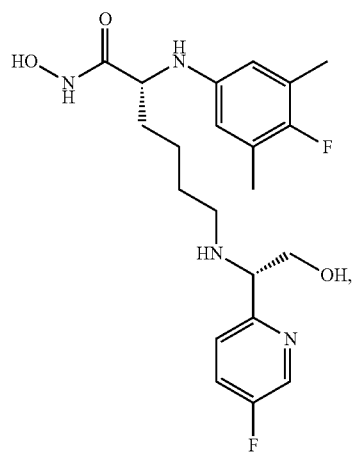

Compound 2

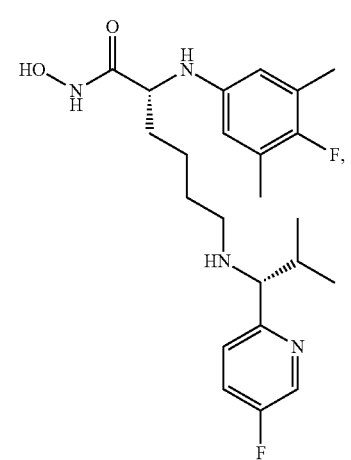

Compound 3

Compound 4
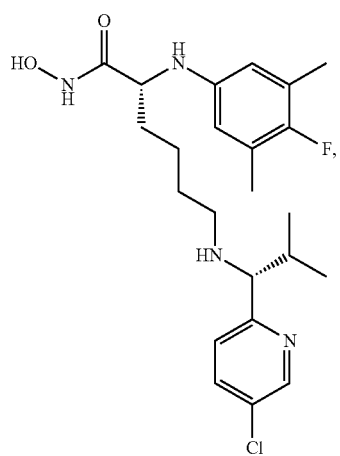
Compound 5
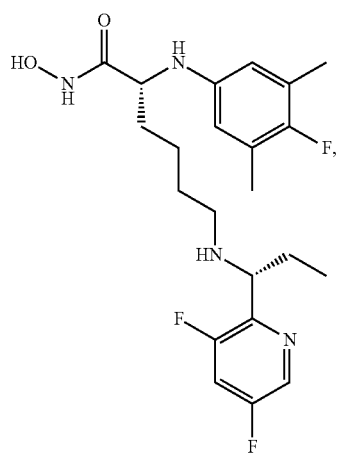
Compound 6
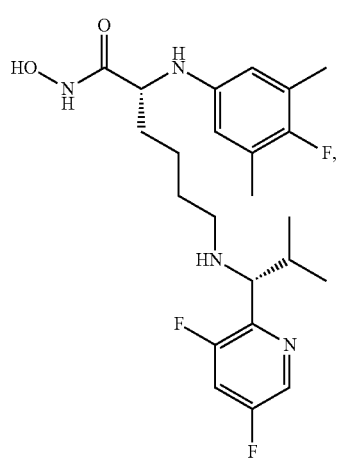
Compound 7
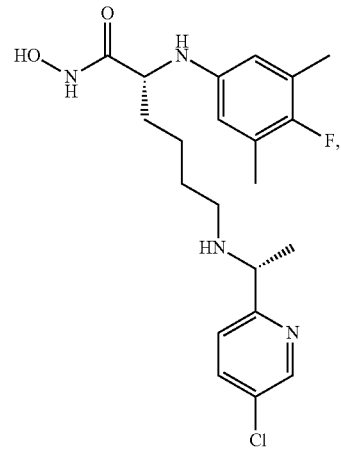
Compound 8
Compound 9

Compound 10
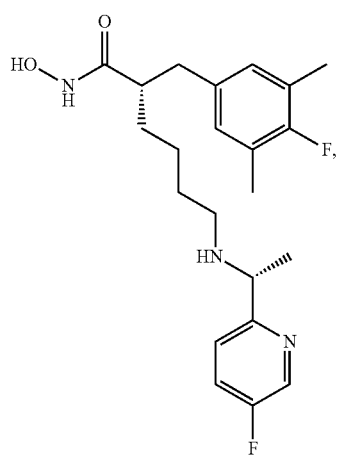
Compound 11
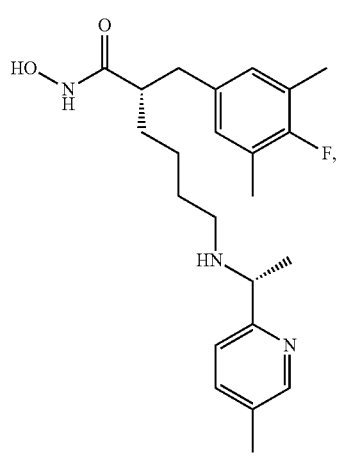
Compound 12
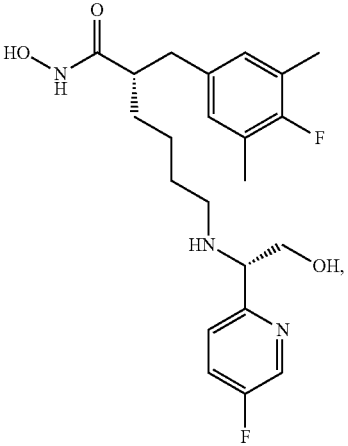
Compound 13
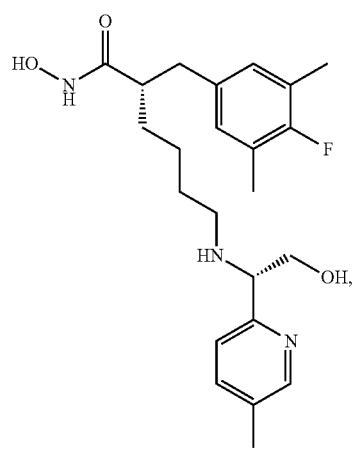
Compound 14
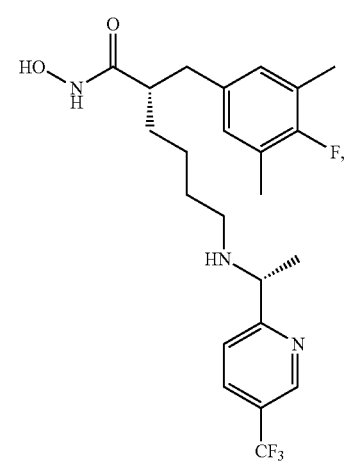
Compound 15
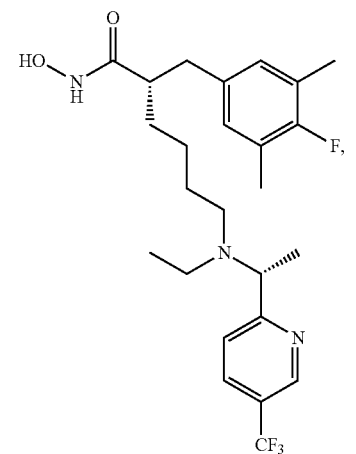

Compound 16
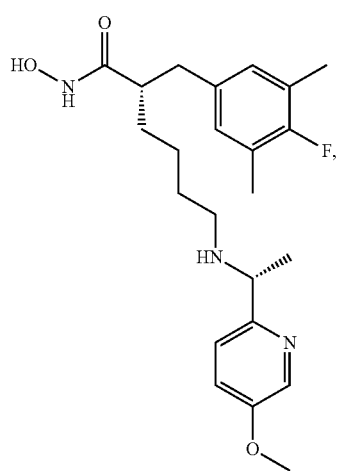
Compound 17
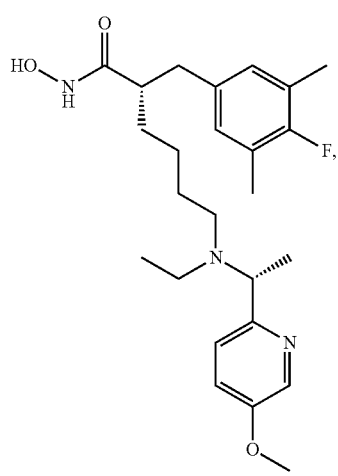
Compound 18
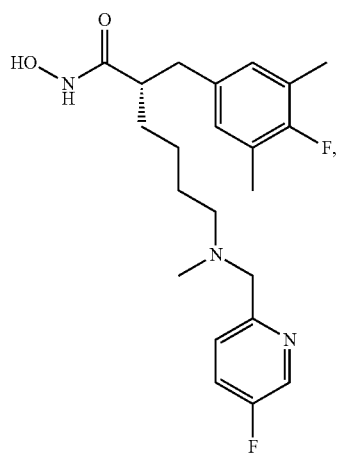
Compound 19
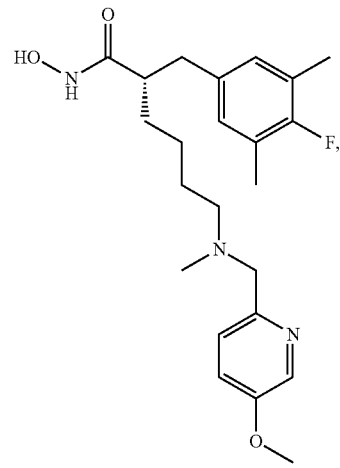
Compound 20
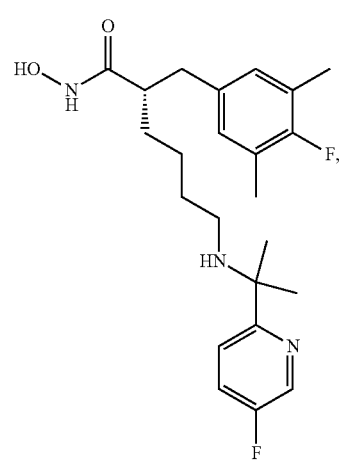
Compound 21
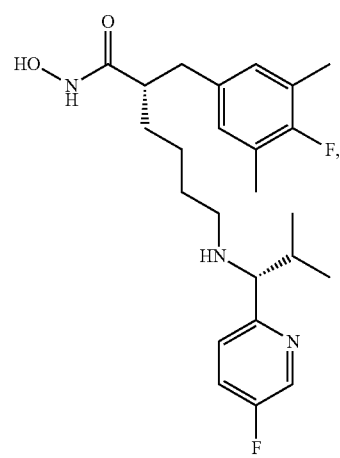

Compound 22
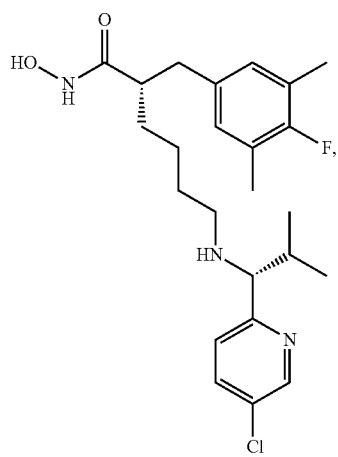
Compound 23
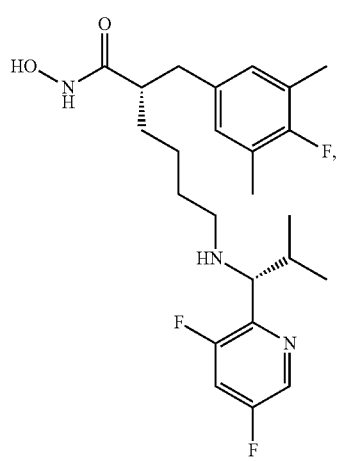
Compound 24
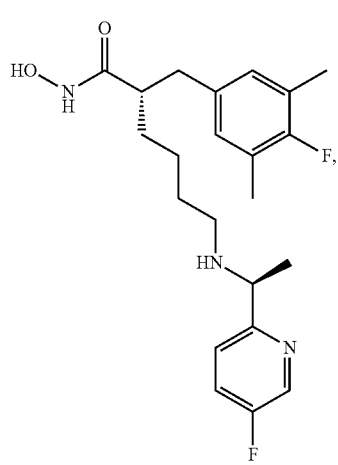
Compound 25
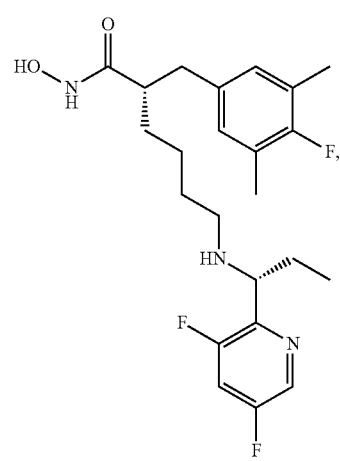
Compound 26
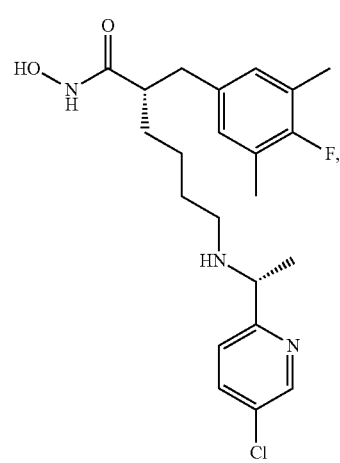
Compound 27
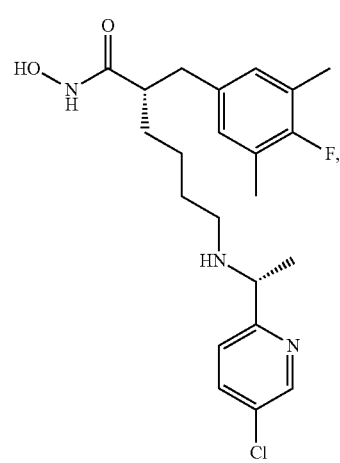

Compound 28
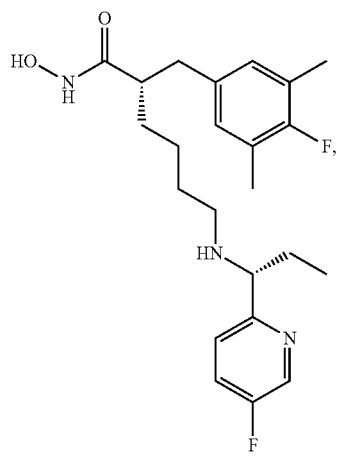
Compound 29
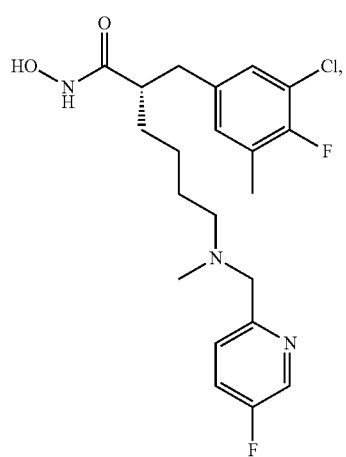
Compound 30
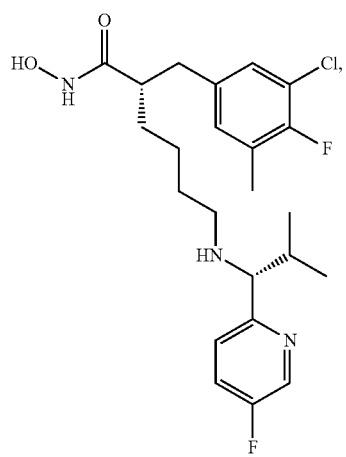
Compound 31
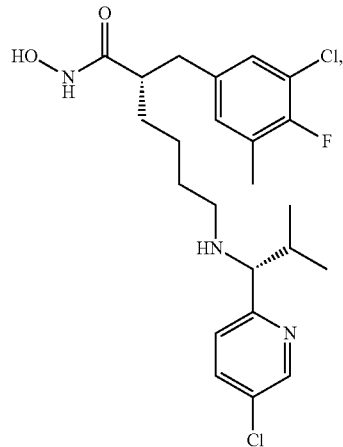
Compound 32
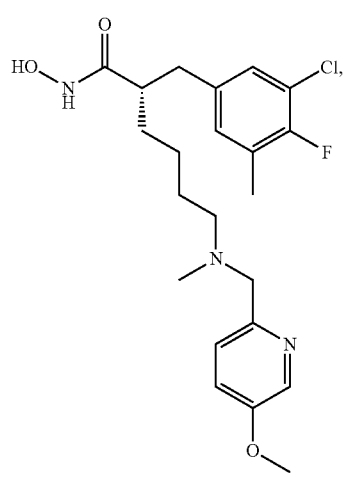
Compound 33
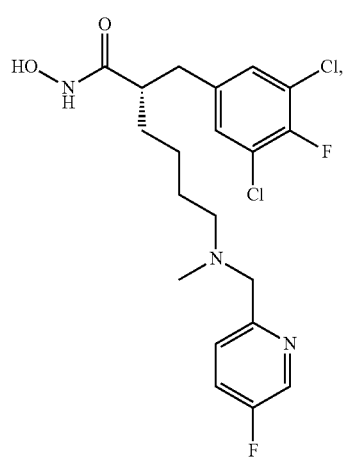

Compound 34
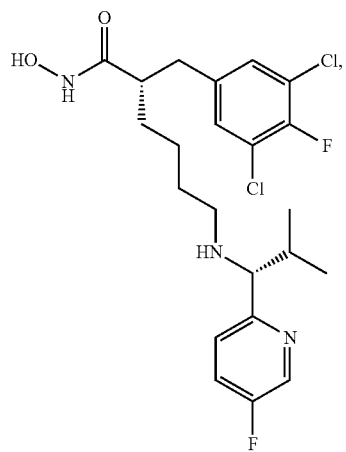
Compound 35
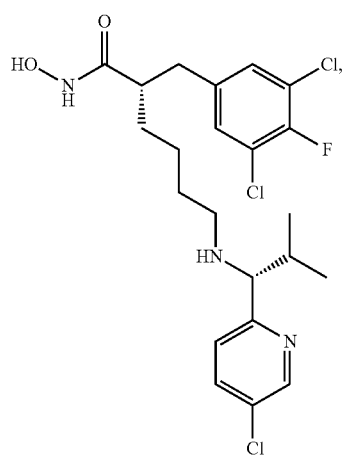
Compound 36
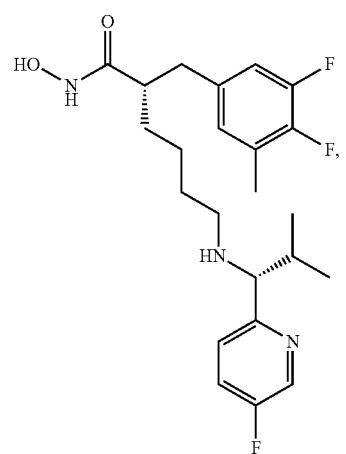
Compound 37
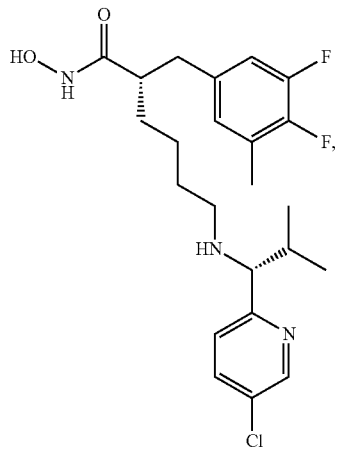
Compound 38
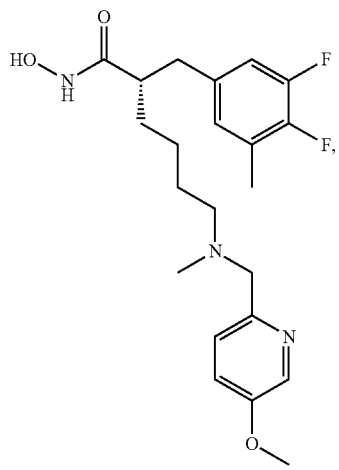
Compound 39
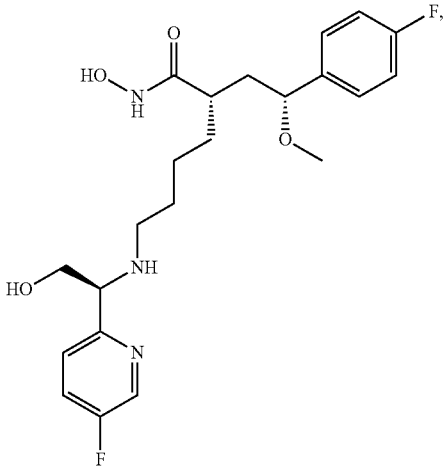

Compound 40
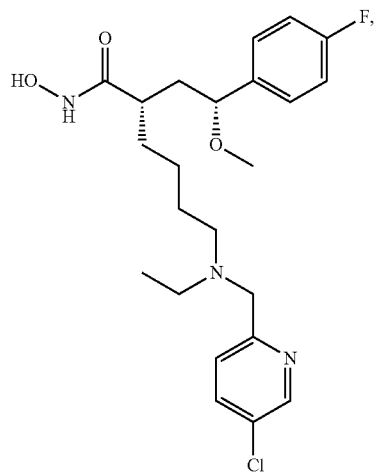
Compound 41
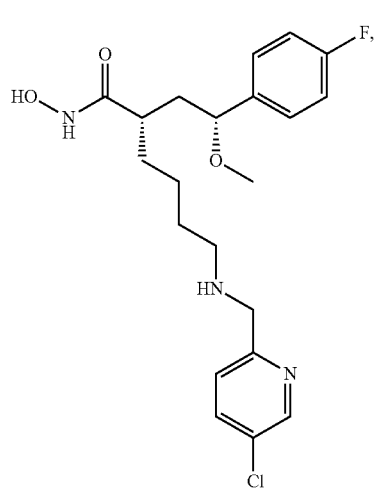
Compound 42
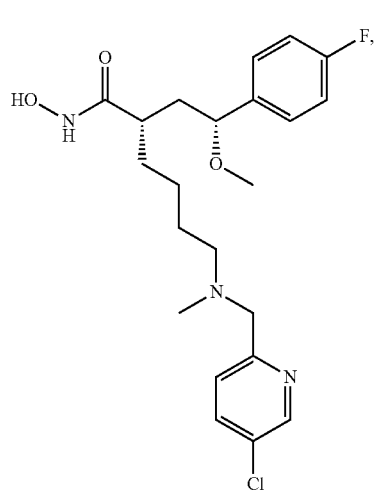
Compound 43
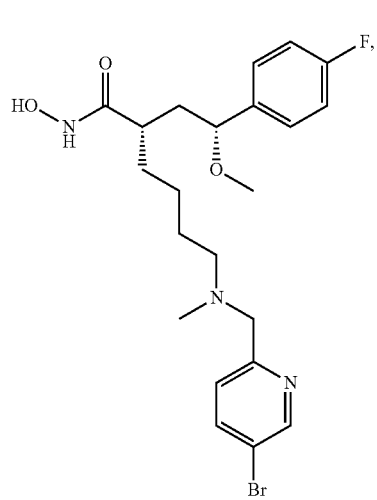
Compound 44
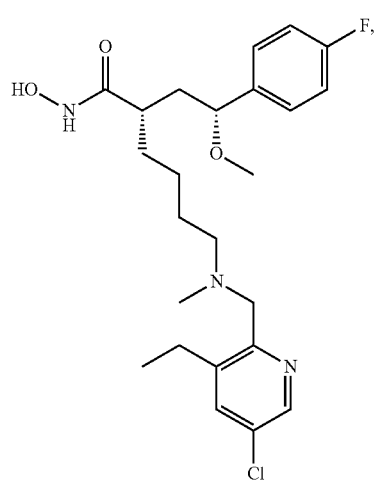
Compound 45
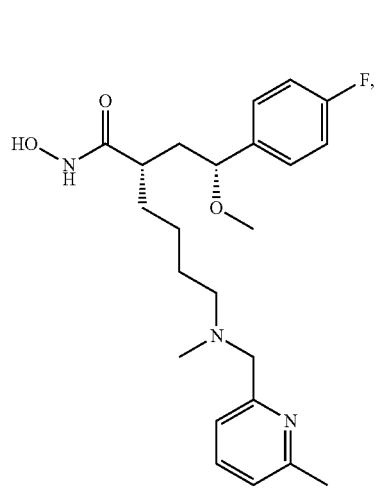

Compound 46
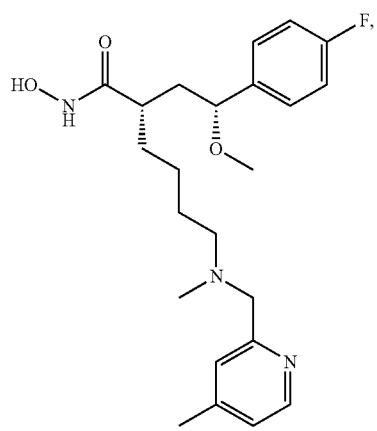
Compound 47
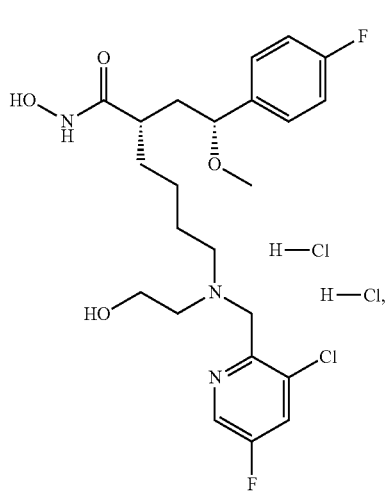
Compound 48
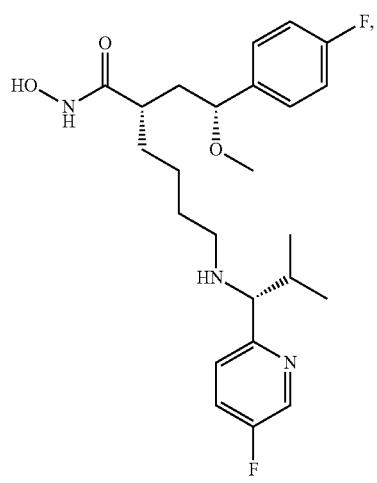
Compound 49
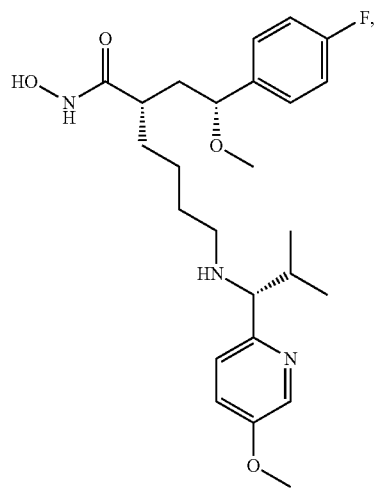
Compound 50
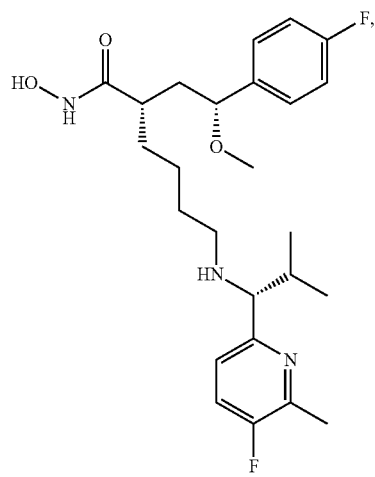
Compound 51
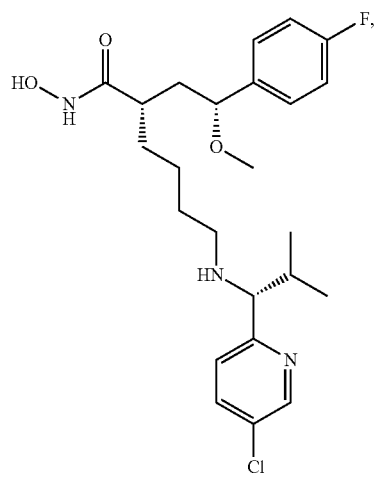

Compound 52
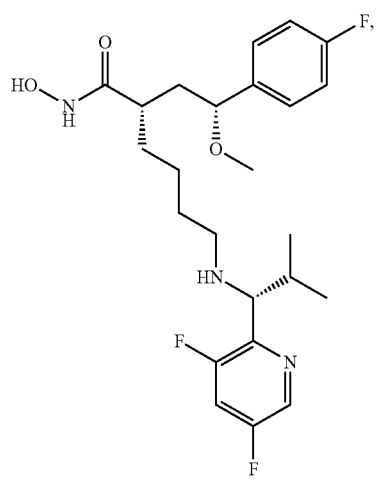
Compound 53
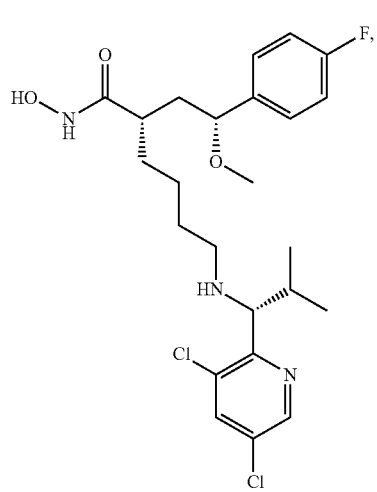
Compound 54
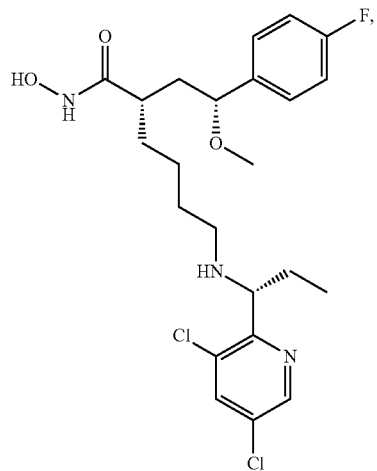
Compound 55
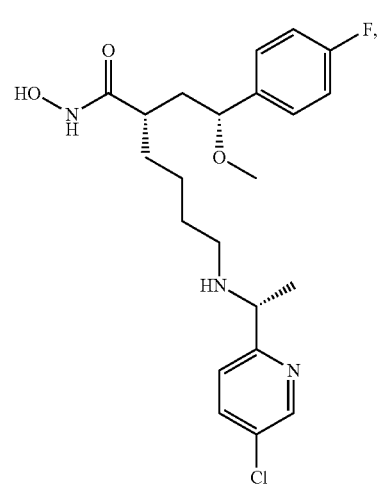
Compound 56
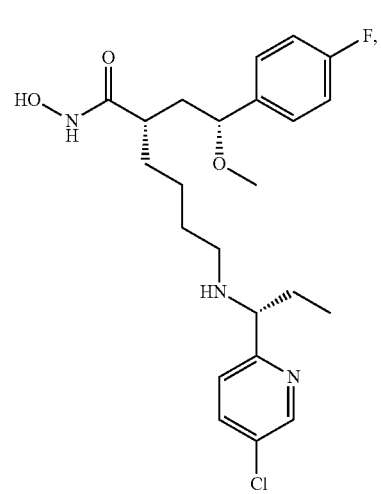
Compound 57, and
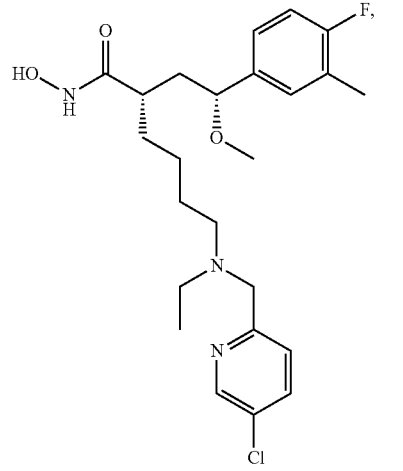

or a pharmaceutically acceptable salt, hydrate or solvate thereof.

19. A pharmaceutical composition comprising a compound according to claim 1 along with a pharmaceutically acceptable carrier.

20. A method of treating a subject exposed to a *Bacillus anthracis* toxin comprising: administering to the subject a therapeutically effective amount of a pharmaceutical composition comprising a compound according to claim 1.

21. The compound of claim 18, wherein the compound is selected from:

or a pharmaceutically acceptable salt hydrate or solvate thereof."

* * * * *